(12) United States Patent  (10) Patent No.: US 7,637,924 B2
Gifford, III et al.  (45) Date of Patent: Dec. 29, 2009

(54) METHODS AND APPARATUS FOR TREATMENT OF PATENT FORAMEN OVALE

(75) Inventors: Hanson Gifford, III, Woodside, CA (US); Mark E. Deem, Mountain View, CA (US); William Malecki, San Francisco, CA (US)

(73) Assignee: Terumo Kabushiki Kaisha, Tokyo (JP)

( * ) Notice: Subject to any disclaimer, the term of this patent is extended or adjusted under 35 U.S.C. 154(b) by 680 days.

(21) Appl. No.: 11/053,274

(22) Filed: Feb. 7, 2005

(65) Prior Publication Data

US 2005/0131460 A1  Jun. 16, 2005

Related U.S. Application Data

(63) Continuation of application No. 10/811,228, filed on Mar. 26, 2004.

(60) Provisional application No. 60/458,854, filed on Mar. 27, 2003, provisional application No. 60/490,082, filed on Jul. 24, 2003, provisional application No. 60/478,035, filed on Jun. 11, 2003.

(51) Int. Cl.
*A61B 17/08* (2006.01)
*A61B 19/00* (2006.01)
(52) U.S. Cl. .................. 606/213; 606/215; 128/898
(58) Field of Classification Search ......... 606/213–216; 128/898
See application file for complete search history.

(56) References Cited

U.S. PATENT DOCUMENTS

| | | | |
|---|---|---|---|
| 2,275,167 A | 3/1942 | Bierman |
| 2,580,628 A | 1/1952 | Welsh |
| 2,888,928 A | 6/1959 | Seiger |
| 3,490,442 A | 1/1970 | Streu |
| 3,862,627 A | 1/1975 | Hans, Sr. |
| 3,874,388 A | 4/1975 | King et al. |
| 3,906,955 A | 9/1975 | Roberts |

(Continued)

FOREIGN PATENT DOCUMENTS

EP 135840 A2 4/1985

(Continued)

OTHER PUBLICATIONS

Australian Government Office Action for App. No. 2004226374, dated Oct. 16, 2008.*

(Continued)

*Primary Examiner*—Michael Peffley
(74) *Attorney, Agent, or Firm*—Oblon, Spivak, McClelland, Maier & Neustadt, L.L.P.

(57) ABSTRACT

Methods and apparatus for treatment of patent foramen ovale (PFO) generally involve use of a catheter having treatment means at its distal end. In some embodiments, the treatment means includes one or more retractable abrasive needles used to abrade tissue adjacent the PFO to induce closure of the PFO. In other embodiments, treatment means includes an energy transmission member or one or more apertures for dispensing a fluid to contact and close the PFO. An exemplary method involves advancing a catheter device to position the distal end adjacent the PFO, exposing a plurality of abrasive needles from the catheter, advancing the needles through the PFO and/or tissue adjacent the PFO, and retracting the needles relative to the PFO to abrade at least a portion of the tissue.

22 Claims, 21 Drawing Sheets

U.S. PATENT DOCUMENTS

| | | |
|---|---|---|
| 4,307,720 A | 12/1981 | Weber, Jr. |
| 4,326,529 A | 4/1982 | Doss et al. |
| 4,473,077 A | 9/1984 | Noiles et al. |
| 4,485,817 A | 12/1984 | Swiggett |
| 4,532,924 A | 8/1985 | Auth et al. |
| 4,556,065 A | 12/1985 | Hoffmann |
| 4,562,838 A | 1/1986 | Walker |
| 4,590,934 A | 5/1986 | Malis et al. |
| 4,682,596 A | 7/1987 | Bales et al. |
| 4,788,975 A | 12/1988 | Shturman et al. |
| 4,798,594 A | 1/1989 | Hillstead |
| 4,832,048 A | 5/1989 | Cohen |
| 4,884,567 A | 12/1989 | Elliott et al. |
| 4,895,565 A | 1/1990 | Hillstead |
| 4,911,159 A | 3/1990 | Johnson et al. |
| 4,919,129 A | 4/1990 | Weber, Jr. et al. |
| 4,929,246 A | 5/1990 | Sinofsky |
| 4,976,711 A | 12/1990 | Parins et al. |
| 4,986,889 A | 1/1991 | Charamathieu et al. |
| 5,041,095 A | 8/1991 | Littrell |
| 5,042,707 A | 8/1991 | Taheri |
| 5,055,100 A | 10/1991 | Olsen |
| 5,056,517 A | 10/1991 | Fenici |
| 5,057,107 A | 10/1991 | Parins et al. |
| 5,071,417 A | 12/1991 | Sinofsky |
| 5,071,418 A | 12/1991 | Rosenbaum |
| 5,078,717 A | 1/1992 | Parins et al. |
| 5,099,827 A | 3/1992 | Melzer et al. |
| RE33,925 E | 5/1992 | Bales et al. |
| 5,125,928 A | 6/1992 | Parins et al. |
| 5,156,608 A | 10/1992 | Troidl et al. |
| 5,156,613 A | 10/1992 | Sawyer |
| 5,171,311 A | 12/1992 | Rydell |
| 5,195,959 A | 3/1993 | Smith |
| 5,196,007 A | 3/1993 | Ellman et al. |
| 5,197,963 A | 3/1993 | Parins |
| 5,207,670 A | 5/1993 | Sinofsky |
| 5,209,756 A | 5/1993 | Seedhom et al. |
| 5,290,278 A | 3/1994 | Anderson |
| 5,292,362 A | 3/1994 | Bass et al. |
| 5,295,955 A | 3/1994 | Rosen et al. |
| 5,300,065 A | 4/1994 | Anderson |
| 5,336,221 A | 8/1994 | Anderson |
| 5,336,252 A | 8/1994 | Cohen |
| 5,342,413 A | 8/1994 | Hirschberg et al. |
| 5,345,935 A | 9/1994 | Hirsch |
| 5,370,675 A | 12/1994 | Edwards et al. |
| 5,380,304 A | 1/1995 | Parker |
| 5,383,917 A | 1/1995 | Desai et al. |
| 5,405,322 A | 4/1995 | Lennox |
| 5,409,479 A | 4/1995 | Dew et al. |
| 5,409,481 A | 4/1995 | Poppas et al. |
| 5,500,012 A | 3/1996 | Brucker et al. |
| 5,505,730 A | 4/1996 | Edwards |
| 5,507,744 A | 4/1996 | Tay et al. |
| 5,540,677 A | 7/1996 | Sinofsky |
| 5,569,239 A | 10/1996 | Sinofsky |
| 5,571,216 A | 11/1996 | Anderson |
| 5,575,772 A | 11/1996 | Lennox |
| 5,584,872 A | 12/1996 | LaFontaine et al. |
| 5,611,794 A | 3/1997 | Sauer et al. |
| 5,620,481 A | 4/1997 | Desai et al. |
| 5,626,607 A | 5/1997 | Malecki et al. |
| 5,662,643 A | 9/1997 | Kung et al. |
| 5,665,109 A | 9/1997 | Yoon |
| 5,669,934 A | 9/1997 | Sawyer |
| 5,693,078 A | 12/1997 | Desai et al. |
| 5,709,224 A | 1/1998 | Behl et al. |
| 5,713,891 A | 2/1998 | Poppas |
| 5,725,522 A | 3/1998 | Sinofsky |
| 5,730,742 A | 3/1998 | Wojciechowicz |
| 5,749,895 A | 5/1998 | Sawyer et al. |
| 5,782,899 A | 7/1998 | Imran |
| 5,814,065 A | 9/1998 | Diaz |
| 5,824,015 A | 10/1998 | Sawyer |
| 5,827,265 A | 10/1998 | Glinsky et al. |
| 5,846,196 A | 12/1998 | Siekmeyer et al. |
| 5,846,261 A * | 12/1998 | Kotula et al. ................. 606/213 |
| 5,855,312 A | 1/1999 | Toledano |
| 5,871,443 A | 2/1999 | Edwards et al. |
| 5,919,200 A | 7/1999 | Stambaugh et al. |
| 5,925,078 A | 7/1999 | Anderson |
| 5,928,266 A | 7/1999 | Kontos |
| 5,931,165 A | 8/1999 | Reich et al. |
| 5,944,738 A | 8/1999 | Amplatz et al. |
| 5,972,023 A | 10/1999 | Tanner et al. |
| 5,972,024 A | 10/1999 | Northrup, III et al. |
| 6,004,316 A | 12/1999 | Laufer |
| 6,012,457 A | 1/2000 | Lesh |
| 6,036,699 A | 3/2000 | Andreas et al. |
| 6,050,994 A | 4/2000 | Sherman |
| 6,056,760 A | 5/2000 | Koike et al. |
| 6,063,081 A | 5/2000 | Mulier et al. |
| 6,063,085 A | 5/2000 | Tay et al. |
| 6,083,223 A | 7/2000 | Baker |
| 6,086,570 A | 7/2000 | Aboul-Hosn et al. |
| 6,086,586 A | 7/2000 | Hooven |
| 6,087,552 A | 7/2000 | Gregory |
| 6,092,528 A | 7/2000 | Edwards |
| 6,132,429 A | 10/2000 | Baker |
| 6,149,660 A | 11/2000 | Laufer et al. |
| 6,156,032 A | 12/2000 | Lennox |
| 6,168,594 B1 | 1/2001 | LaFontaine et al. |
| 6,211,335 B1 | 4/2001 | Owen et al. |
| 6,221,068 B1 | 4/2001 | Fried et al. |
| 6,236,875 B1 | 5/2001 | Bucholz |
| 6,257,241 B1 | 7/2001 | Wampler |
| 6,290,674 B1 | 9/2001 | Roue et al. |
| 6,302,898 B1 | 10/2001 | Edwards et al. |
| 6,323,037 B1 | 11/2001 | Lauto et al. |
| 6,325,798 B1 | 12/2001 | Edwards et al. |
| 6,355,030 B1 | 3/2002 | Aldrich et al. |
| 6,358,246 B1 | 3/2002 | Behl et al. |
| 6,375,668 B1 | 4/2002 | Gifford et al. |
| 6,383,198 B1 | 5/2002 | Hamilton |
| 6,391,048 B1 | 5/2002 | Ginn et al. |
| 6,391,049 B1 | 5/2002 | McNally et al. |
| 6,398,779 B1 | 6/2002 | Buysee et al. |
| 6,398,782 B1 | 6/2002 | Pecor et al. |
| 6,398,797 B2 | 6/2002 | Bombard et al. |
| 6,401,720 B1 | 6/2002 | Stevens et al. |
| 6,409,720 B1 | 6/2002 | Hissong et al. |
| 6,413,254 B1 | 7/2002 | Hissong et al. |
| 6,419,669 B1 | 7/2002 | Frazier et al. |
| 6,423,057 B1 | 7/2002 | He et al. |
| 6,436,088 B2 | 8/2002 | Frazier et al. |
| 6,451,013 B1 | 9/2002 | Bays et al. |
| 6,456,865 B2 | 9/2002 | Samson |
| 6,458,100 B2 | 10/2002 | Roue et al. |
| 6,475,213 B1 | 11/2002 | Whayne et al. |
| 6,482,224 B1 * | 11/2002 | Michler et al. ............... 606/219 |
| 6,514,250 B1 | 2/2003 | Jahns et al. |
| 6,558,314 B1 | 5/2003 | Adelman et al. |
| 6,558,382 B2 | 5/2003 | Jahns et al. |
| 6,562,037 B2 | 5/2003 | Paton et al. |
| 6,583,117 B2 | 6/2003 | Owen et al. |
| 6,584,360 B2 | 6/2003 | Francischelli et al. |
| 6,589,237 B2 | 7/2003 | Woloszko |
| 6,606,523 B1 | 8/2003 | Jenkins |
| 6,641,604 B1 | 11/2003 | Adelman |
| 6,645,202 B1 | 11/2003 | Pless et al. |
| 6,645,225 B1 * | 11/2003 | Atkinson .................... 606/213 |
| 6,648,897 B2 | 11/2003 | Hamilton |
| 6,652,518 B2 | 11/2003 | Wellman |

| | | | | | |
|---|---|---|---|---|---|
| 6,669,693 B2 | 12/2003 | Friedman | 2005/0070923 A1 | 3/2005 | McIntosh |
| 6,676,685 B2 | 1/2004 | Pedros et al. | 2005/0075665 A1 | 4/2005 | Brenzel et al. |
| 6,682,546 B2 | 1/2004 | Amplatz | 2005/0119675 A1 | 6/2005 | Adams et al. |
| 6,692,450 B1 | 2/2004 | Coleman | 2005/0125032 A1 | 6/2005 | Whisenant et al. |
| 6,702,835 B2 | 3/2004 | Ginn | 2005/0171526 A1 | 8/2005 | Rioux et al. |
| 6,712,804 B2 | 3/2004 | Roue et al. | 2005/0187568 A1 | 8/2005 | Klenk et al. |
| 6,712,836 B1 | 3/2004 | Berg et al. | 2005/0192626 A1 | 9/2005 | Widomski et al. |
| 6,716,211 B2 | 4/2004 | Mulier et al. | 2005/0192627 A1 | 9/2005 | Whisenant et al. |
| 6,726,718 B1 | 4/2004 | Carlyle et al. | 2005/0192654 A1 | 9/2005 | Chanduszko et al. |
| 6,730,108 B2 | 5/2004 | Van Tassel et al. | 2005/0209636 A1 | 9/2005 | Widomski et al. |
| 6,733,498 B2 | 5/2004 | Paton et al. | 2005/0216054 A1 | 9/2005 | Widomski et al. |
| 6,736,810 B2 | 5/2004 | Hoey et al. | 2005/0251201 A1 | 11/2005 | Roue et al. |
| 6,755,790 B2 | 6/2004 | Stewart et al. | 2005/0256532 A1 | 11/2005 | Nayak et al. |
| 6,770,072 B1 | 8/2004 | Truckai et al. | 2005/0267495 A1 | 12/2005 | Ginn et al. |
| 6,776,784 B2 * | 8/2004 | Ginn .................... 606/151 | 2005/0267525 A1 | 12/2005 | Chanduszko |
| 6,790,218 B2 | 9/2004 | Jayaraman | 2006/0009762 A1 | 1/2006 | Whayne |
| 6,846,319 B2 | 1/2005 | Ginn et al. | 2006/0036284 A1 | 2/2006 | Blaeser et al. |
| 6,887,238 B2 | 5/2005 | Jahns | 2006/0052821 A1 | 3/2006 | Abbott et al. |
| 6,893,431 B2 | 5/2005 | Naimark et al. | 2006/0069408 A1 | 3/2006 | Kato |
| 6,893,442 B2 | 5/2005 | Whayne | 2006/0079870 A1 | 4/2006 | Barry |
| 6,918,908 B2 | 7/2005 | Bonner et al. | 2006/0079887 A1 | 4/2006 | Buysse et al. |
| 6,926,716 B2 | 8/2005 | Baker et al. | 2006/0173510 A1 | 8/2006 | Besio et al. |
| 6,929,644 B2 | 8/2005 | Truckai et al. | 2007/0088355 A9 | 4/2007 | Auth |
| 6,932,812 B2 | 8/2005 | Crowley et al. | | | |
| 6,939,348 B2 | 9/2005 | Malecki et al. | | | |
| 6,946,134 B1 | 9/2005 | Rosen et al. | FOREIGN PATENT DOCUMENTS | | |
| 6,960,205 B2 | 11/2005 | Jahns et al. | EP | 199694 A2 | 10/1986 |
| 7,025,756 B2 | 4/2006 | Frazier et al. | EP | 0265532 A1 | 5/1988 |
| 7,094,215 B2 | 8/2006 | Davison et al. | EP | 0375556 A1 | 6/1990 |
| 7,165,552 B2 | 1/2007 | Deem et al. | EP | 0428812 A1 | 5/1991 |
| 7,238,182 B2 | 7/2007 | Swoyer et al. | EP | 0947165 A1 | 10/1999 |
| 2001/0020166 A1 | 9/2001 | Daly et al. | GB | 1260919 | 1/1972 |
| 2001/0037129 A1 | 11/2001 | Thill | GB | 1550676 | 8/1979 |
| 2001/0051803 A1 | 12/2001 | Desai et al. | GB | 2 359 024 A | 8/2001 |
| 2002/0128672 A1 | 9/2002 | Dinger et al. | WO | WO 85/00018 A1 | 1/1985 |
| 2002/0143322 A1 | 10/2002 | Haghighi | WO | WO 87/04081 | 1/1986 |
| 2002/0156472 A1 | 10/2002 | Lee et al. | WO | WO 90/04352 A1 | 5/1990 |
| 2003/0028189 A1 | 2/2003 | Woloszko et al. | WO | WO 91/15996 A1 | 10/1991 |
| 2003/0045893 A1 | 3/2003 | Ginn | WO | WO 92/04864 A1 | 4/1992 |
| 2003/0045901 A1 | 3/2003 | Opolski | WO | WO 93/05705 A1 | 4/1993 |
| 2003/0050665 A1 | 3/2003 | Ginn | WO | WO 93/15791 A1 | 8/1993 |
| 2003/0065364 A1 | 4/2003 | Wellman et al. | WO | WO 94/00178 A1 | 1/1994 |
| 2003/0069570 A1 | 4/2003 | Witzel | WO | WO 98/07375 | 2/1998 |
| 2003/0078578 A1 | 4/2003 | Truckai et al. | WO | WO 99/18862 A1 | 4/1999 |
| 2003/0092988 A1 | 5/2003 | Markin | WO | WO 99/18864 A1 | 4/1999 |
| 2003/0093071 A1 | 5/2003 | Hauck et al. | WO | WO 99/18870 | 4/1999 |
| 2003/0120268 A1 | 6/2003 | Bertolero et al. | WO | WO 99/18871 | 4/1999 |
| 2003/0144652 A1 | 7/2003 | Baker et al. | WO | WO 99/23959 A1 | 5/1999 |
| 2003/0144694 A1 | 7/2003 | Chanduszko et al. | WO | WO 99/49788 A | 10/1999 |
| 2003/0158551 A1 | 8/2003 | Paton et al. | WO | WO 00/07506 A2 | 2/2000 |
| 2003/0199868 A1 | 10/2003 | Desai et al. | WO | WO 00/09027 A1 | 2/2000 |
| 2003/0208232 A1 | 11/2003 | Blaeser et al. | WO | WO 01/13810 A1 | 3/2001 |
| 2003/0225421 A1 | 12/2003 | Peavey et al. | WO | WO 01/78596 A1 | 10/2001 |
| 2003/0233091 A1 | 12/2003 | Whayne et al. | WO | WO 01/82778 A | 11/2001 |
| 2004/0059347 A1 | 3/2004 | Hamilton | WO | WO 03/022159 A1 | 3/2003 |
| 2004/0092973 A1 | 5/2004 | Chanduszko et al. | WO | WO 03/022160 A1 | 3/2003 |
| 2004/0098031 A1 | 5/2004 | Van der Burg et al. | WO | WO 03/026496 A2 | 4/2003 |
| 2004/0098042 A1 | 5/2004 | Devellian et al. | WO | WO 03/053493 | 7/2003 |
| 2004/0098121 A1 * | 5/2004 | Opolski .................... 623/3.1 | WO | WO 03/071957 A2 | 9/2003 |
| 2004/0102721 A1 | 5/2004 | McKinley | WO | WO 03/082076 | 10/2003 |
| 2004/0143292 A1 | 7/2004 | Marino et al. | WO | WO 03/094742 A1 | 11/2003 |
| 2004/0153057 A1 | 8/2004 | Davison | WO | WO 2004/019791 A2 | 3/2004 |
| 2004/0153098 A1 | 8/2004 | Chin et al. | WO | WO 2004/043266 A2 | 5/2004 |
| 2004/0176799 A1 | 9/2004 | Chanduszko et al. | WO | WO 2004/069055 A2 | 8/2004 |
| 2004/0220596 A1 | 11/2004 | Frazier et al. | WO | WO 2004/082532 A1 | 9/2004 |
| 2004/0243122 A1 | 12/2004 | Auth et al. | WO | WO 2004/091411 A2 | 10/2004 |
| 2004/0249398 A1 | 12/2004 | Ginn | WO | WO 2005/006990 A2 | 1/2005 |
| 2005/0021059 A1 | 1/2005 | Cole et al. | WO | WO 2005/027753 A1 | 3/2005 |
| 2005/0033288 A1 | 2/2005 | Auth et al. | WO | WO 2005/034738 A2 | 4/2005 |
| 2005/0033327 A1 | 2/2005 | Gainor et al. | WO | WO 2005/046487 A1 | 12/2005 |
| 2005/0055050 A1 | 3/2005 | Alfaro | WO | WO 2005/074814 A2 | 8/2005 |
| 2005/0065506 A1 | 3/2005 | Phan | | | |
| 2005/0065509 A1 | 3/2005 | Coldwell et al. | | | |

WO    WO 2005/115256 A    12/2005

OTHER PUBLICATIONS

People's Republic of China Decision on Rejection for App. No. 200480011741.1, dated Jan. 16, 2009.*

Australian Government Office Action for App. No. 2004226374, dated May 29, 2009.*

Anzola et al., "Potential Source of Cerebral Embolism in Migraine with Aura," *Neurology* (1999) 52(8): 1622.

De Castro et al., "Morphological and Functional Characteristics of Patent Foramen Ovale and Their Embolic Implications," *Stroke* (Oct. 2002), pp. 2407-2413.

Cordis Corporation, Cordis Ducor® Lumeleo™ Electorode Catheters [brochure], Cordis Corporation, (Dec. 1984), 2 pages.

Del Sette, "Migraine with Aura and Right-to-Left Shunt on Transcranial Doppler: A Case Control Study," *Cerebrovas Dis* (1998) 8:327-330.

Gillette, "Catheter Ablation in Dysrhythmias," *Cardio*, (Mar. 1984), pp. 67-69.

Ho et al., "Morphological Features Pertinent to Interventional Closure of Patent Oval Foramen," *J Interventional Cardiology*, vol. 16 No. 1, (2003), pp. 33-34.

Kennedy et al., "High-burst-Strength, feedback-controlled bipolar vessel sealing," *Surg Endosc* (1998) 12:876-878.

Koenig et al., "Role of Intracardiac Echocardiographic Guidance in Transcatheter Closure of Atrial Septal Defects and Patent Foramen Ovale Using the Amplatzer® Device," *J. Interventional Cardiology*, (2003) 16 (1): 51-62.

Morady, "Transvenous Catheter Ablation of a Posterospetial Accessory Pathway in a Patient with the Wolff Parkinson-White Syndrome," *The New England Journal of Medicine*, (Mar. 15, 1984), 310(11): 705-707.

Morandi et al., "Transcatheter Closure of Patent Foramen Ovale: A New Migraine Treatment?" *J Interventional Cardiology*, (2003), 16(1): 39-42.

Pfleger, "Haemodynamic Quantification of Different Provocation Manoeuvres by Simultaneous Measurement of Right and Left Atrial Pressure: Implications for the Echocardiographic Detection of Persistent Foramen Ovale," *Eur J Echocardiography* (2001) 2: 88-93.

Polgar et al., "A New Technique for Closed-Chest Human His Bundle Ablation Using Suction Electrode Catheter and DC Shock," In: Perez Gomez F, ed. *Cardiac Pacing Electrophysiology Tachyarrhythmias*. Madrid, Spain: Grouz Publishers; 1985:1582-1586.

Polgar et al., "Comparison of Two Different Techniques for Closed-Chest His Bundle Ablation," In: Perez Gomez F, ed. *Cardiac Pacing Electrophysiology Tachyarrhythmias*. Madrid, Spain: Grouz Publishers; 1985:1578-1587.

Polgar, "Closed Chested Ablation of His Bundle: A New Technique Using Suction Electorde Catheter and DC Shock," *Nachdruck Aus: Cardio Pacing*, (1983), pp. 883-890.

Stuart, "What's All the Flap About PFO Closure?," *Start-Up: Windhover's Review of Emerging Medical Ventures*, (Nov. 10, 2004), pp. 9-14.

Sztajzel et al., "Patent Foramen Ovale, a Possible Cause of Symptomatic Migraine: A Study of 74 Patients with Acute Ischemic Stroke," *Cerebrovas Dis* (2002) 13: 102-106.

Thomas, "Patent Foramen Ovale with Right-to-left Shunting: Echocariographic Alternatives," *Eur J Echocariography* (2001) 2:74-75.

Wilmhurst et al., "Effect on Migraine of Closure of Cardiac Right-to-Left Shunts to Prevent Recurrence of Decompression Illness of Illness or Stroke or for Haemodynamic Reasons," *The Lancet*, vol. 356, (Nov. 11, 2000), pp. 1648-1651.

Wilmhurst et al., "Relationship between Migraine and Cardiac and Pulmonary Right to Left Shunts," *Clinical Science* (2001) 100:215-220.

Athiraman et al., "Selective Photothermal Tissue Interaction Using 805-nm Laser and Indocyanine Green in Tissue Welding," *Journal of X-Ray Science and Technology*, vol. 12, No. 2, (2004), pp. 117-126.

Fenner et al., "Shear Strength of Tissue Bonds as a Function of Bonding Temperature: A Proposed Mechanism for Laser-Assisted Tissue Welding," *Lasers in Medical Science*, vol. 7, (1992), pp. 39-43.

Godlewski et al., "Applications and Mechanisms of Laser Tissue Welding in 1995: Review," *Proc. SPIE*, vol. 2623, (Jan. 1996) pp. 334-341.

Olson et al., "Developing An Animal Model for the Study of Fusion Using RF Energy," *Proc. SPIE*, vol. 5312, (2004), pp. 147-161.

Ott et al., "Comparative in Vitro Study of Tissue Welding Using a 808 nm Diode Laser and a Ho:YAG laser," *Lasers Med Sci*, vol. 16, (2001) pp. 260-266.

Poppas et al., "Temperature-Controlled Laser Photocoagulation of Soft Tissue: in Vivo Evaluation Using a Tissue Welding Model," Lasers Surg Med., vol. 18, No. 4, (1996), pp. 335-344.

Stewart et al., "Laser Assisted Vascular Welding with Real Time Temperature Control," Lasers Surg Med., vol. 19, No. 1, (1996), pp. 9-16.

Tang et al., "Quantitative Changes in Collagen Levels Following 830-nm Diode Laser Welding," Lasers Surg Med., vol. 22, No. 4, (1998), pp. 207-211.

Tang et al, "Morphologic Changes in Collagen Fibers after 830 nm Diode Laser Welding," Lasers Surg Med., vol. 21, No. 5 (1997), pp. 438-443.

Besio et al., "Quantizing the Depth of Bioelectrical Sources for Non-Invasive 3D Imaging," IJBEM, vol. 7, No. 2, (2005), 4 pages total.

* cited by examiner

METHODS AND APPARATUS FOR TREATMENT OF PATENT FORAMEN OVALE

CROSS-REFERENCES TO RELATED APPLICATIONS

This application is a continuation of U.S. patent application Ser. No. 10/811,228, filed Mar. 26, 2004, which claims priority from U.S. Provisional Patent Application No. 60/458,854, filed on Mar. 27, 2003; No. 60/478,035, filed on Jun. 11, 2003, and No. 60/490,082, filed on Jul. 24, 2003, the full disclosures of which are incorporated herein by reference. This application is related to U.S. patent application Ser. No. 10/665,974, filed on Sep. 16, 2003, now U.S. Pat. No. 7,165,552; Ser. No. 10/679,245, filed Oct. 2, 2003, now U.S. Pat. No. 6,939,348; and Ser. No. 10/787,532, filed Feb. 25, 2004, now U.S. Pat. No. 7,186,251, the full disclosures of which are incorporated herein by reference.

BACKGROUND OF THE INVENTION

The invention generally relates to medical apparatus and methods. More specifically, the invention relates to apparatus and methods for treatment of patent foramen ovale (PFO).

Fetal blood circulation is much different than adult circulation. Because fetal blood is oxygenated by the placenta, rather than the fetal lungs, blood is generally shunted away from the lungs to the peripheral tissues through a number of vessels and foramens that remain patent (i.e., open) during fetal life and typically close shortly after birth. For example, fetal blood passes directly from the right atrium through the foramen ovale into the left atrium, and a portion of blood circulating through the pulmonary artery trunk passes through the ductus arteriosus to the aorta. This fetal circulation is shown in attached FIG. 1.

At birth, as a newborn begins breathing, blood pressure in the left atrium rises above the pressure in the right atrium. In most newborns, a flap of tissue closes the foramen ovale and heals together. In approximately 20,000 babies born each year in the US, the flap of tissue is missing, and the hole remains open as an atrial septal defect (ASD). In a much more significant percentage of the population (estimates range from 5% to 20% of the entire population), the flap is present but does not heal together. This condition is known as a patent foramen ovale (PFO). Whenever the pressure in the right atrium rises above that in the left atrium, blood pressure can push this patent channel open, allowing blood to flow from the right atrium to the left atrium.

Patent foramen ovale has long been considered a relatively benign condition, since it typically has little effect on the body's circulation. More recently, however, it has been found that a significant number of strokes may be caused at least in part by PFO. In some cases, stroke may occur because a PFO allows blood containing small thrombi to flow directly from the venous circulation to the arterial circulation and into the brain, rather than flowing to the lungs where the thrombi can become trapped and gradually dissolved. In other cases, thrombi might form in the patent channel of the PFO itself and become dislodged when the pressures cause blood to flow from the right atrium to the left atrium. It has been estimated that patients with PFOs who have already had cryptogenic strokes have a 4% risk per year of having another stroke.

Further research is currently being conducted into the link between PFO and stroke. At the present time, if someone with a PFO has two or more strokes, the healthcare system in the U.S. may reimburse a surgical or other interventional procedure to definitively close the PFO. It is likely, however, that a more prophylactic approach would be warranted to close PFOs to prevent the prospective occurrence of a stroke. The cost and potential side-effects and complications of such a procedure must be low, however, since the event rate due to PFOs is relatively low. In younger patients, for example, PFOs sometimes close by themselves over time without any adverse health effects.

Another highly prevalent and debilitating condition—chronic migraine headaches—has also been linked with PFO. Although the exact link has not yet been explained, PFO closure has been shown to eliminate or significantly reduce migraine headaches in many patients. Again, prophylactic PFO closure to treat chronic migraine headaches might be warranted if a relatively non-invasive procedure were available.

Currently available interventional therapies for PFO are generally fairly invasive and/or have potential drawbacks. One strategy is simply to close a PFO during open heart surgery for another purpose, such as heart valve surgery. This can typically be achieved via a simple procedure such as placing a stitch or two across the PFO with vascular suture. Performing open heart surgery purely to close an asymptomatic PFO or even a very small ASD, however, would be very hard to justify.

A number of interventional devices for closing PFOs percutaneously have also been proposed and developed. Most of these devices are the same as or similar to atrial septal defect (ASD) closure devices. They are typically "clamshell" or "double umbrella" shaped devices which deploy an area of biocompatible metal mesh or fabric (ePTFE or Dacron, for example) on each side of the atrial septum, held together with a central axial element, to cover the PFO. This umbrella then heals into the atrial septum, with the healing response forming a uniform layer of tissue or "pannus" over the device. Such devices have been developed, for example, by companies such as Nitinol Medical Technologies, Inc. (Boston, Mass.) and AGA Medical, Inc. (White Bear Lake, Minn.). U.S. Pat. No. 6,401,720 describes a method and apparatus for thoracoscopic intracardiac procedures which may be used for treatment of PFO.

Of particular interest, the use of a catheter having a balloon with abrasive elements has been proposed for abrading the inner surfaces of a PFO to cause an area of thrombogenesis. See U.S. Pat. No. 5,919,200. Over time, it is hoped that the area will form a scar and close the PFO. Other patents of interest include U.S. Pat. Nos. 6,056,760, 6,482,224 and 6,702,835 and PCT Publication No. WO98/07375. Published patent applications of interest include U.S. Publication Nos. 2003/0045893 and 2003/0225421 and PCT Publication Nos. WO 03/053493 and WO 03/082076.

Although available devices may work well in some cases, they also face a number of challenges. Relatively frequent causes of complications include, for example, improper deployment, device embolization into the circulation and device breakage. In some instances, a deployed device does not heal into the septal wall completely, leaving an exposed tissue which may itself be a nidus for thrombus formation. Furthermore, the currently available devices are generally complex and expensive to manufacture, making their use for prophylactic treatment of PFO impractical. In addition, it is sometimes difficult to insert a catheter or guidewire directly through the lumen of the PFO using currently available percutaneously inserted catheters.

Therefore, it would be advantageous to have improved methods and apparatus for treating a PFO. Ideally, such methods and apparatus would help seal the PFO while leaving little or no foreign material in the body. Also ideally, such methods and apparatus would be relatively simple to manufacture and use, thus rendering prophylactic treatment of PFO, such as for stroke prevention, a viable option. It would also be advantageous to have a device which could effect closure of a PFO without requiring insertion of a catheter through the PFO. At least some of these objectives will be met by the present invention.

BRIEF SUMMARY OF THE INVENTION

Methods and apparatus for treatment of patent foramen ovale (PFO) generally involve use of a catheter having treatment means at its distal end. In some embodiments, the treatment means includes one or more retractable abrasive needles used to abrade tissue adjacent the PFO to induce closure of the PFO. In some embodiments, treatment means may alternatively or additionally include an energy transmission member, such as a radiofrequency, ultrasound, microwave, laser or cryogenic energy transmission member. In other embodiments, treatment means may include or one or more apertures for dispensing a fluid to contact and close the PFO.

In some embodiments, treatment means comprises one or more closure devices, such as one or more clips, staples, patches, a self-closing attachment members, spiral needles or the like. Some closure devices have at least a portion that resides within the PFO and applies lateral force against tissue at opposite sides of the PFO, thus bringing tissue between the opposed sides together. Closure devices may optionally be implanted using energy and/or energy-mediated solders or tissue glues. Optionally, the closure devices may be biodegradable or may be formed from non-degradable materials. In exemplary devices, a delivery catheter may include a backstop for positioning in the left atrium to provide a working surface to facilitate closure device deployment. The backstop may be removable after closure of the PFO.

Methods generally involve advancing the catheter to position its distal end near the PFO and using the treatment means to close the PFO in any one of a variety of ways. In a first embodiment one or more abrasive needles or other abrasive elements are used to abrade or otherwise traumatize tissue adjacent the PFO to induce closure of the PFO. In other embodiments, the PFO is closed with a closure device which is optionally secured to tissue with energy and/or a solder or tissue glue. The closure device may be a plug that physically covers the PFO. Alternatively, the device may be self-closing to capture and close the PFO.

In one aspect, a method of treating a patent foramen ovale comprises: advancing a catheter device having a proximal end, a distal end and at least one abrasive needle near the distal end through vasculature of a patient to position the distal end adjacent the patent foramen ovale; exposing a plurality of abrasive needles from the catheter; advancing the exposed abrasive needles through the patent foramen ovale; and retracting the abrasive needles relative to the patent foramen ovale to abrade at least a portion of tissue adjacent the patent foramen ovale. In some embodiments, advancing the catheter comprises advancing through at least one of a femoral vein, an iliac vein, an inferior vena cava, a brachial vein, an axial vein, a subclavian vein, and a superior vena cava of the patient. In some embodiments, advancing the catheter comprises advancing over a guidewire.

In some embodiments, exposing the abrasive needles involves retracting a catheter body of the catheter to expose the needles out of an opening in the catheter body at or near the distal end of the catheter. Alternatively, exposing the abrasive needles may involve advancing the needles relative to the catheter body. In some embodiments, advancing the abrasive needles comprises passing at least one needle through tissue immediately adjacent the PFO. Advancing the abrasive needles may involve advancing the needles relative to the catheter, advancing the catheter itself to advance the needles, or both in various embodiments. In one embodiment, retracting the abrasive needles comprises abrading at least a portion of the patent foramen ovale with serrated edges of the needles. In any embodiment, the abrasive needles may be retracted and advanced as many times as desired. Optionally, any embodiment may include visualization of the PFO and/or tissue surrounding the PFO using one or more visualization devices.

In another aspect, a method of treating a PFO comprises: advancing a catheter device having a proximal end, a distal end and at least one abrasive needle near the distal end through vasculature of a patient to position the distal end adjacent the PFO; exposing the at least one abrasive needle from the catheter; advancing the at least one exposed abrasive needle through heart wall tissue adjacent the PFO, for example through the tissue of the septum secundum and/or septum primum; and retracting the at least one abrasive needle relative to the tissue to abrade at least a portion of the tissue. This method may include any of the optional steps or elements mentioned above.

In still another aspect, a method of treating a patent foramen ovale involves: advancing a catheter device having a proximal end, a distal end and at least one abrasive needle near the distal end through vasculature of a patient to position the distal end adjacent the PFO; exposing a first abrasive needle from the catheter such that the exposed first abrasive needle extends through at least part of the PFO; exposing at least a second abrasive needle from the catheter such that the exposed second abrasive needle extends through the PFO; and retracting the first and second abrasive needles relative to the PFO to abrade at least a portion of tissue adjacent the PFO. Optionally, the method may further include exposing a third abrasive needle from the catheter such that the exposed third abrasive needle extends through the PFO and retracting the third abrasive needle relative to the PFO to abrade at least a portion of tissue adjacent the patent foramen ovale. The method may still further include exposing a fourth abrasive needle from the catheter such that the exposed fourth abrasive needle extends through the PFO and retracting the fourth abrasive needle relative to the PFO to abrade at least a portion of tissue adjacent the PFO. Again, any of the features, steps or elements described above may be applied to this method.

In another aspect, a method of treating PFO involves advancing a catheter device having a proximal end, a distal end and an energy transmission member near the distal end through vasculature of a patient to position the distal end adjacent the PFO, and transmitting energy from the energy transmission member to contact tissue adjacent the PFO to induce closure of the PFO. The transmitted energy may comprise, for example, laser energy, radio frequency energy, ultrasound energy, microwave energy, cryogenic energy, removal of energy via cooling or the like. The closure may be effected immediately by application of energy, or secondarily as a result of healing after the application of energy. In some embodiments, the energy transmission members may comprise needles which are advanced into the tissue adjacent the PFO. In some of these embodiments, the needles may be delivered in a manner which draws the tissue together prior to the application of energy.

In another aspect, a method of treating PFO comprises advancing a catheter device having a proximal end, a distal end and at least one aperture near the distal end through vasculature of a patient to position the distal end adjacent the PFO, and dispensing at least one fluid from the at least one aperture to contact tissue adjacent the PFO to induce closure of the PFO. The fluid, for example, may include a biocompatible fluid such as an acid or an adhesive. In some embodiments, the method may include the inflation of a balloon or other member adjacent the distal end to isolate the area of the atrial septum from blood flow, thus increasing the time the fluid is in the vicinity of the PFO.

In another aspect of the invention, a method of treating a patent foramen ovale in a heart involves advancing a catheter device having a proximal end and a distal end through vasculature of a patient to position the distal end adjacent the patent foramen ovale and delivering a closure device at least partially through the patent foramen ovale to induce closure of the patent foramen ovale. In this method, a portion of the closure device disposed within the patent foramen ovale applies lateral force against tissues at opposite sides of the patent foramen ovale to bring tissue between the sides together. Optionally, the method may further include transmitting energy such as but not limited to laser energy, radio frequency energy, ultrasound energy, microwave energy, cryogenic energy or removal of energy via cooling from the catheter to secure the closure device in the patent foramen ovale.

Also optionally, the method may include allowing the closure device to collapse and draw the patent foramen closed. In some embodiments, the method includes positioning a backstop apparatus in the left atrium as the closure device is deployed. Some embodiments include delivering a tissue solder material which is set by the energy to adhere the closure device to the tissue. Other embodiments may include inflating an expandable balloon coupled with the catheter device near the distal end to deploy the closure device within the patent foramen ovale.

In some embodiments, delivering the closure device involves releasing a left atrial portion of the closure device from the catheter device such that it contacts tissue adjacent the patent foramen ovale from within in a left atrium of the heart and releasing a right atrial portion of the closure device from the catheter device such that it contacts tissue adjacent the patent foramen ovale from within in a left atrium of the heart. In such embodiments, a bridging portion of the closure device extends through the patent foramen ovale between the left atrial portion and the right atrial portion and applies the lateral force against the tissues at the opposite sides of the patent foramen ovale. In some embodiments, the left atrial portion is released before the right atrial portion, while in others the right atrial portion is released before the left atrial portion. Some embodiments may further include removing the closure device from the patent foramen ovale through using the catheter device and repositioning the closure device at least partially through the patent foramen ovale and in contact with tissue adjacent the patent foramen ovale. In some embodiments, removing the closure device comprises advancing the catheter device over the closure device to straighten the closure device and retracting the catheter device to remove the closure device from the patent foramen ovale. In some embodiments, the left atrial portion is straightened before the right atrial portion, and in other embodiments the right atrial portion is straightened before the left atrial portion.

In another aspect of the invention, a method for treating a patent foramen ovale involves disposing at least a portion of a closure device within the patent foramen ovale and applying lateral, oppositely directed force to tissues at opposite sides of the patent foramen ovale, using the portion of the closure device disposed in the patent foramen ovale, so as to bring a septum primum and a septum secundum between the opposite sides into contact. Optionally, the method may also comprise placing at least one device to maintain the contact between the primum and secundum. Such a method may optionally further comprise applying energy to maintain the contact between the primum and secundum. In some embodiments tissue solder may be introduced to maintain the contact between primum and secundum.

In another aspect of the invention, a method of treating a patent foramen ovale in a heart involves advancing a catheter device having a proximal end and a distal end through vasculature of a patient to position the distal end adjacent the patent foramen ovale and delivering a self-closing closure device from the catheter to contact tissues adjacent the patent foramen ovale. In this method, the delivered self-closing closure device closes to bring together the tissues the patent foramen ovale. In some embodiments, for example, delivering the self-closing closure device comprises driving multiple tissue attachment members coupled with a self-closing stent into the tissues.

In another aspect, a method for treating a patent foramen ovale involves attaching a closure device to a limbus of a fossa ovalis of the heart and allowing a portion of the closure device to hang from the limbus to cover an opening of the patent foramen ovale. Such a method may optionally further involve applying energy to secure the closure device.

In another aspect of the invention, a method of treating a patent foramen ovale in a heart includes: advancing an elongate catheter device through septum primum tissue near the patent foramen ovale; adjusting a retractable delivery arm from the catheter device, the delivery arm coupled with a distal end of the catheter device via a universal joint; and manipulating the catheter device to deploy a spiral needle from the delivery arm into tissues adjacent the patent foramen ovale to bring the tissues together. In some embodiments, the spiral needle is deployed through septum primum and septum secundum tissues. Manipulating the catheter device, for example, may involve turning or twisting the device about its longitudinal axis.

In yet another aspect, an apparatus for treating PFO comprises an elongate catheter body having a proximal end and a distal end and at least one retractable abrasive needle movable between a retracted position wherein the needle resides wholly within the catheter body and a deployed position wherein at least a portion of the needle extends through an opening in the catheter body adjacent the distal end. In some embodiments, the catheter body is passable over a guidewire. Also in some embodiments, the at least one retractable abrasive needle comprises at least one serrated edge for abrading tissue adjacent the PFO. Optionally, the at least one retractable abrasive needle comprises multiple needles. In some embodiments, each of the multiple needles is individually retractable into the catheter body. Also in some embodiments, the at least one retractable abrasive needle is movable relative to the catheter body to extend the at least one needle through the PFO and retract the needle back through the foramen ovale. In some embodiments, the apparatus may include a visualization device for facilitating visualization of a PFO.

In another aspect, apparatus for treating a PFO includes an elongate catheter body having a proximal end and a distal end and at least one energy transmission member coupled with the catheter body adjacent the distal end for transmitting energy to contact tissue adjacent the PFO to induce closure of the PFO. As mentioned above, the energy transmission member may transmit any suitable form of energy, such as but not limited to laser energy, radio frequency energy, ultrasound energy, microwave energy or cryogenic energy. In some embodiments, the apparatus for delivering energy into or adjacent the PFO may comprise one or more needles, which may be movable relative to the catheter body and which may or may not be serrated. In some of these embodiments, the needles may be designed to draw the tissue of the PFO together as well as to deliver energy.

In another aspect, apparatus for treating a PFO comprises an elongate catheter body having a proximal end and a distal end and at least one aperture in the catheter body adjacent the distal end for dispensing at least one fluid to contact tissue adjacent the PFO to induce closure of the PFO. As mentioned, any suitable fluid may be used, such as but not limited to a biocompatible fluid such as an acid or an adhesive. In some embodiments, this apparatus may include an inflatable balloon or other means adjacent the distal tip of the catheter to isolate the area of the atrial septum from blood flow, thus increasing the residence time of the fluid in the area of the PFO.

In another aspect of the invention, an apparatus for treating a PFO includes an elongate catheter body having a proximal end and a distal end and at least one closure device deployable from the catheter body. Specifically, the closure device attaches to tissue adjacent the PFO and self-closes to bring the tissues together. In some embodiments, the closure device is biodegradable. In some embodiments, the closure device comprises an expandable, self-closing stent coupled with a plurality of tissue attachment members, such as but not limited to tissue piercing needles. In some embodiments, the closure device includes a portion extending within the PFO to apply lateral force to tissue at opposite sides of the PFO, thus bringing together tissue between the opposite sides. The catheter body may be passable over a guidewire. Embodiments may optionally include at least one visualization device coupled with the catheter body near the distal end for visualizing the PFO and tissue surrounding the PFO. Some embodiments may include at least one energy transmission member coupled with the catheter body adjacent the distal end for transmitting energy to contact tissue adjacent the PFO. Any suitable energy may be used.

In another aspect, an apparatus for treating a PFO comprises a clip expandable from a first dimension to a second larger dimension sized to engage the tissue of the PFO. The clip in the larger dimension applies lateral force to tissue at opposite sides of the PFO to bring tissues between the opposite sides together. Also, the clip can revert or be made to revert to its first dimension.

In another aspect, apparatus for treating a PFO comprises an elongate catheter body having a proximal end and a distal end and at least one force application member coupled with the distal end for applying lateral force to opposite sides of the PFO, thus bringing tissues between the opposite sides into contact. In some embodiments, the distal end includes at least two arms which deflect laterally to engage the edges of the PFO. Alternatively or additionally, the distal end may include a detachable closure device. The distal end may also optionally include energy delivery means. Such embodiments may further include means to deliver tissue solder or adhesive. The apparatus may also include means to deliver a closure device. For example, the closure device may comprise at least one staple, clip, tissue solder, adhesive or the like.

In another aspect, an apparatus for treating a PFO comprises an attachment member for attaching to a limbus of a fossa ovalis of the PFO and a covering member coupled with the attachment member for extending from the limbus to cover an opening of the PFO. In some embodiments, the covering member comprises a support structure and a mesh covering the support structure. The support structure may comprise, for example, a wire frame, such as multiple Nitinol loops. In some embodiments, energy is applied to secure the device to the limbus and/or other tissues adjacent the PFO. Optionally, the device may further include means for introducing tissue solder or adhesive. In some embodiments, the attachment member is configured to penetrate the tissue of the limbus. In one embodiment, the attachment member comprises opposable jaws.

In another aspect of the invention, an apparatus for treating a patent foramen ovale includes: an elongate catheter configured to pierce through septum primum tissue adjacent the patent foramen ovale; a retractable delivery arm coupled with a distal end of the elongate catheter at a universal joint; and a spiral needle coupled with and deployable from the retractable delivery arm. Turning the catheter deploys the spiral needle into tissue adjacent the patent foramen ovale. In some embodiments, for example, the spiral needle is configured to pierce through septum primum tissue and septum secundum tissue to bring the septum primum and septum secundum together.

These and other aspects and embodiments are described in detail below, with reference to the attached drawing figures.

DETAILED DESCRIPTION OF THE INVENTION

Methods and apparatus of the invention generally provide for treating tissue adjacent a patent foramen ovale (PFO) to cause closure of the foramen. The methods and devices typically include a catheter device which can be advanced through the vasculature of a patient to position the distal end of the catheter near the PFO to provide treatment. Treatment means disposed at or near the distal end of the catheter can then be used to treat at least a portion of the heart wall tissue surrounding the PFO, to cause the PFO to close. In many embodiments, the treatment means is used to cause trauma to the tissues surrounding the PFO and the trauma then induces a response in the tissues which causes the PFO to close. In one embodiment, the treatment means includes one or more abrasive needles having at least one abrasive surface, such as a serrated edge. Such needles may be retractable into (and extendable out of) the body of the catheter. In other embodiments, the treatment means may involve an energy transmission means, such as a laser, ultrasound, RF or microwave transmitter. In still other embodiments, the treatment means may comprise one or more apertures at or near the distal end of the catheter for dispensing a fluid designed to induce closure of the PFO.

Figure 1:
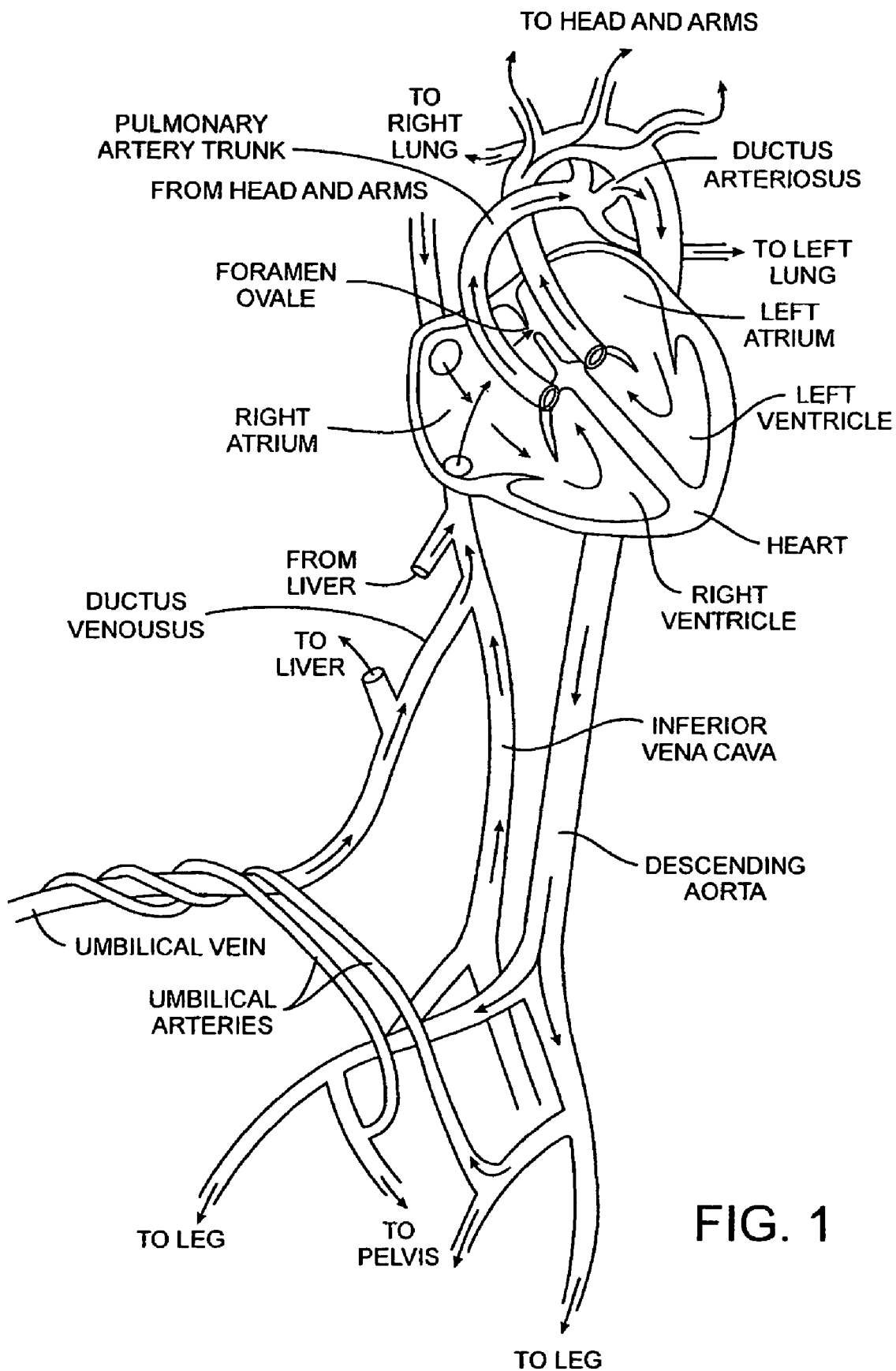
FIG. 1 is a diagram of the fetal circulation.
Figure 2:
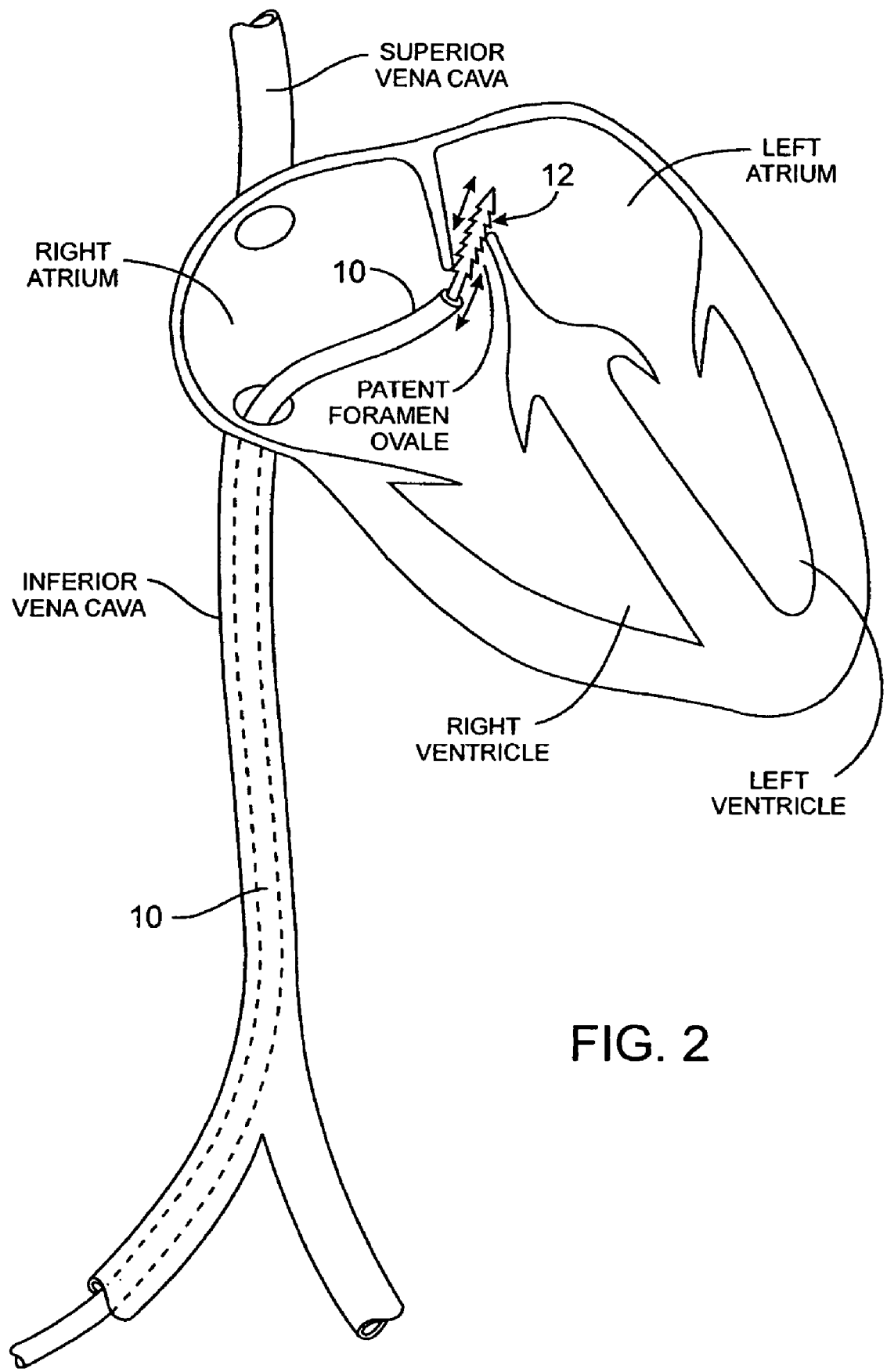
FIG. 2 is a diagram of a catheter apparatus having a needle according to an embodiment of the present invention, the catheter passing through the inferior vena cava and right atrium and through the patent foramen ovale.

Referring now to FIG. 2, an embodiment of a catheter 10 having a retractable abrasive needle 12 is shown in a position for treatment of a PFO. In one embodiment, catheter 10 is introduced percutaneously, for example via the femoral vein and inferior vena cava, using a sheath and/or other introducer device(s). Generally, various embodiments of catheter 10 may be introduced via any suitable vasculature or any other suitable route, such as via a brachial vein, subclavian vein, iliac vein, the superior vena cava and/or the like. In some embodiments, catheter 10 may be advanced over a movable guidewire, such as a standard guidewire of diameter in the range from about 0.038" to about 0.014". Typically (though not necessarily), needle 12 is retractable so that catheter 10 may be advanced with needle 12 in a retracted position within the body of catheter 10. Once the distal end of catheter 10 is in a position for use, needle 12 may then be extended through an aperture at or near the distal end of the catheter body.

Once needle 12 is extended, it may be used to abrade tissue adjacent the PFO. In one embodiment, needle 12 may be similar to a pre-shaped Brockenbrough needle, which is commonly used to make trans-septal punctures. Needle 12 may include any suitable means for abrading tissue. In some embodiments, for example, needle 12 may have one or more surfaces or edges that are serrated, toothed, covered with abrasive material such as a sandpaper-like material, or the like. In other embodiments, the surface of needle 12 may be coated with a drug or chemical that, when it contacts the tissue of the atrial septum surrounding the PFO, causes a reaction in the tissue which leads to PFO closure. Generally, needle 12 is moved through the PFO and/or through tissue adjacent the PFO and is then drawn back through the PFO and/or tissue to cause abrasion. In some cases it is possible to extend needle 12 through the PFO itself, while in other cases it may be difficult to locate the PFO and/or the extend needle 12 through the foramen. In these latter cases, needle 12 may be extended through tissue of the atrial septum adjacent the PFO and then retracted to cause the desired abrasion. Thus, placement of needle 12 through the PFO itself is not always necessary. Obviously, needle 12 may be advanced and retracted through the PFO and/or tissue adjacent the PFO as many times as desired to achieve a desired amount of tissue abrasion. In some instances, a physician may use one or more visualization techniques to asses progress of the abrasion process to determine when a desired level is achieved.

Although the proximal end of catheter 10 is not shown in FIG. 2, this may have any suitable configuration and may include any type or number of actuator(s). For example, in embodiments having one or more needles 12, there will typically be at least one actuator at or near the proximal end of catheter 10 for advancing and/or retracting needle 12. In embodiments having multiple needles 12, the needles may be individually advanced and retracted via separate actuators or may be advanced and retracted together via a common actuator in various embodiments. Other features of the proximal end of catheter 10 may include, but are not limited to, a guidewire port, a port for providing introduction of one or more fluids, means for coupling catheter with an energy source, and/or the like.

Needle 12 may generally be moved through/across the PFO and/or tissue adjacent the PFO by any suitable means. In some embodiments, as mentioned above, needle 12 may be moved relative to the catheter body of catheter 10, for example by retracting and advancing needle 12 relative to catheter 10 using a proximal actuator. In other embodiments, needle 12 may be moved across/through the PFO by simply advancing and retracting catheter 10. And of course a combination of these movements may be used in some embodiments, so that needle 12 may be manipulated relative to catheter 10 and may also be advanced and retracted through the PFO by manipulating catheter 10 as a whole.

Figure 3:
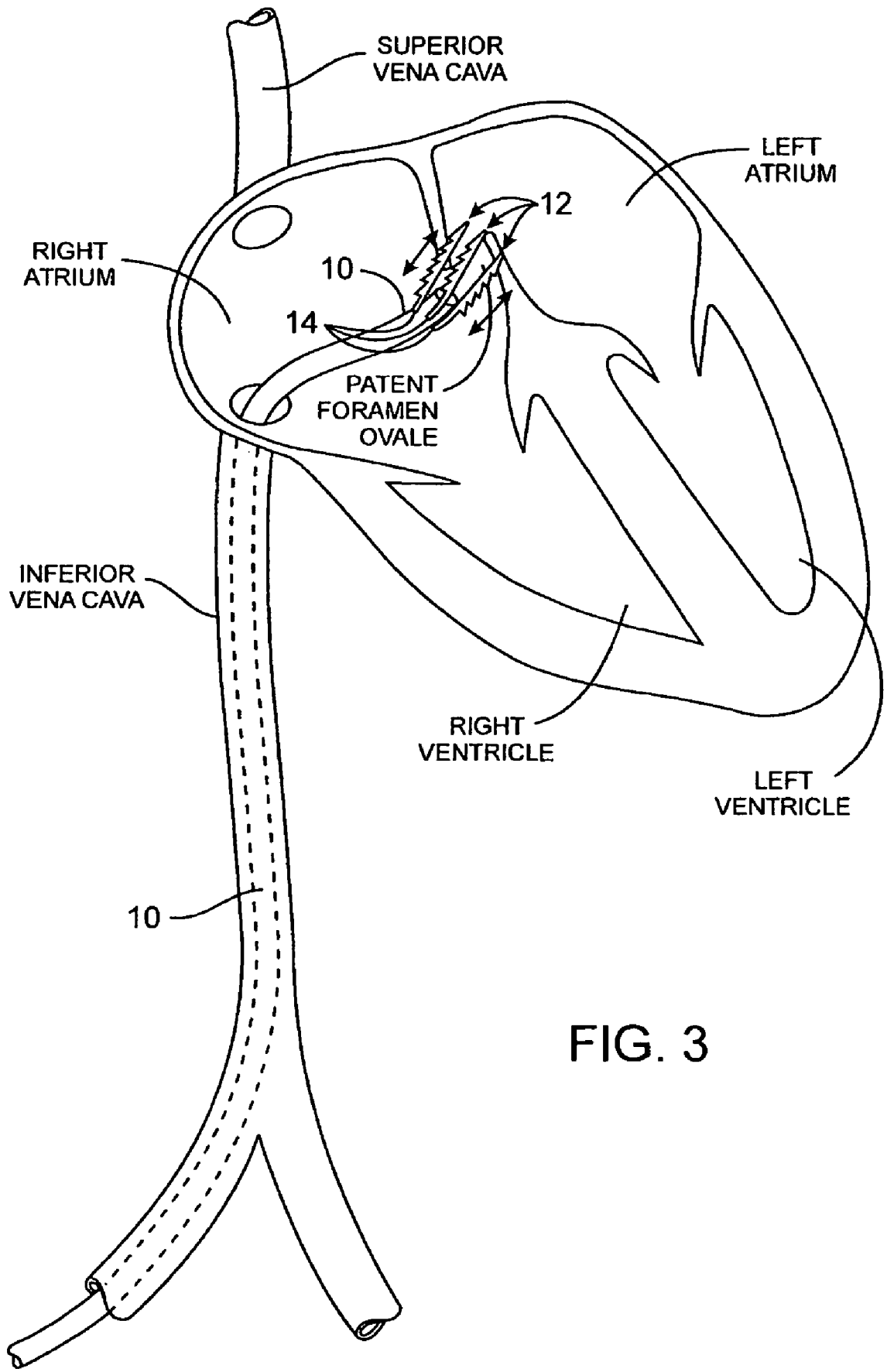
FIG. 3 is a diagram of a catheter apparatus having multiple needles according to an embodiment of the present invention, the catheter passing through the inferior vena cava and right atrium and through the patent foramen ovale.

Referring now to FIG. 3, another embodiment of catheter 10 is shown having multiple (in this case three) needles 12. Such an embodiment may be used in much the same way as the embodiment described above having one needle 12. Here, the three needles 12 extend out of catheter 10 via three separate apertures 14 in the catheter body near the distal end of catheter 10. Generally, in any given embodiment, needles 12 may extend from catheter 10 via one or multiple apertures in the extreme distal end of catheter 10, near the distal end or the like. Any suitable configuration is contemplated. In the embodiment in FIG. 3, two needles 12 are shown extending through atrial septal tissue adjacent the PFO and one needle 12 extends through the foramen itself. Again, any combination of piercing through atrial septal tissue, abrading septal tissue by extending through the PFO and the like is contemplated.

The embodiment pictured in FIG. 3 demonstrates that needles 12 can have any suitable configuration. In this embodiment, needles 12 have one serrated edge, in contrast to needle 12 in FIG. 2 that is serrated on at least two surfaces. Again, any suitable configuration for abrasive needles 12 is contemplated within the scope of the invention. In some embodiments, needles may have a curved or undulating configuration. In some embodiments, needles may be predominantly rigid, while in other embodiments they may flexible. Various embodiments of needles may be serrated edges, toothed edges, abrasive sandpaper-like surfaces, and/or any other suitable means for abrading tissue.

Methods for using the devices described above have already been described somewhat. Generally, a method involves advancing a catheter device having a proximal end, a distal end and at least one abrasive needle near the distal end through vasculature of a patient to position the distal end adjacent the PFO, exposing the abrasive needle from the catheter, advancing the needle through the PFO and/or tissue adjacent the PFO, and retracting the needle relative to the PFO and/or tissue to abrade at least a portion of tissue adjacent the PFO. In some embodiments, a patient may be treated before and/or after a PFO treatment procedure with appropriate anti-clotting agents, such as aspirin, coumadin, 2B-3A inhibitors or the like, to prevent clots from forming on the healing tissue and embolizing during the healing period. As discussed above, access to the patient's heart and PFO may be gained by any suitable means, but will often involve percutaneous access via the femoral vein and inferior vena cava or other veins.

After advancing the catheter to position the distal end near the PFO and/or at any other stage in the method for PFO treatment, a physician may use one or more visualization devices to image the PFO. For example, the physician may inject contrast into the right atrium while the patient is coughing, performing a Valsalva maneuver or other actions to cause blood flow through the PFO, and one or more images may be acquired. In some embodiments, after one or more images are taken of the PFO, a guidewire may be placed through the PFO and catheter 10 may be advanced over the guidewire. In some cases it will be possible to advance the guidewire and catheter 10 through the PFO, while in other cases this will be difficult. In the latter cases, the physician may position the distal end of catheter 10 near the PFO and advance one or more needles 12 through the tissue of the atrial septum surrounding or adjacent to the PFO. In embodiments including multiple needles 12, the needles 12 may be advanced all at once or one at a time. As described above, some needles 12 have serrations on one or more edge or surface which may allow for relatively easy advancement of needles 12 while providing sufficient abrasion on retraction of needles 12. As shown by the two-headed arrows in FIGS. 2 and 3, needles 12 may be advanced and retracted any number of times to achieve a desired amount of abrasion. In some embodiments, the amount of abrasion may be confirmed through visualization of the PFO and surrounding tissues. When abrasion is complete, needles 12 may be retracted into catheter 10 and catheter may be removed from the patient.

Figure 4:
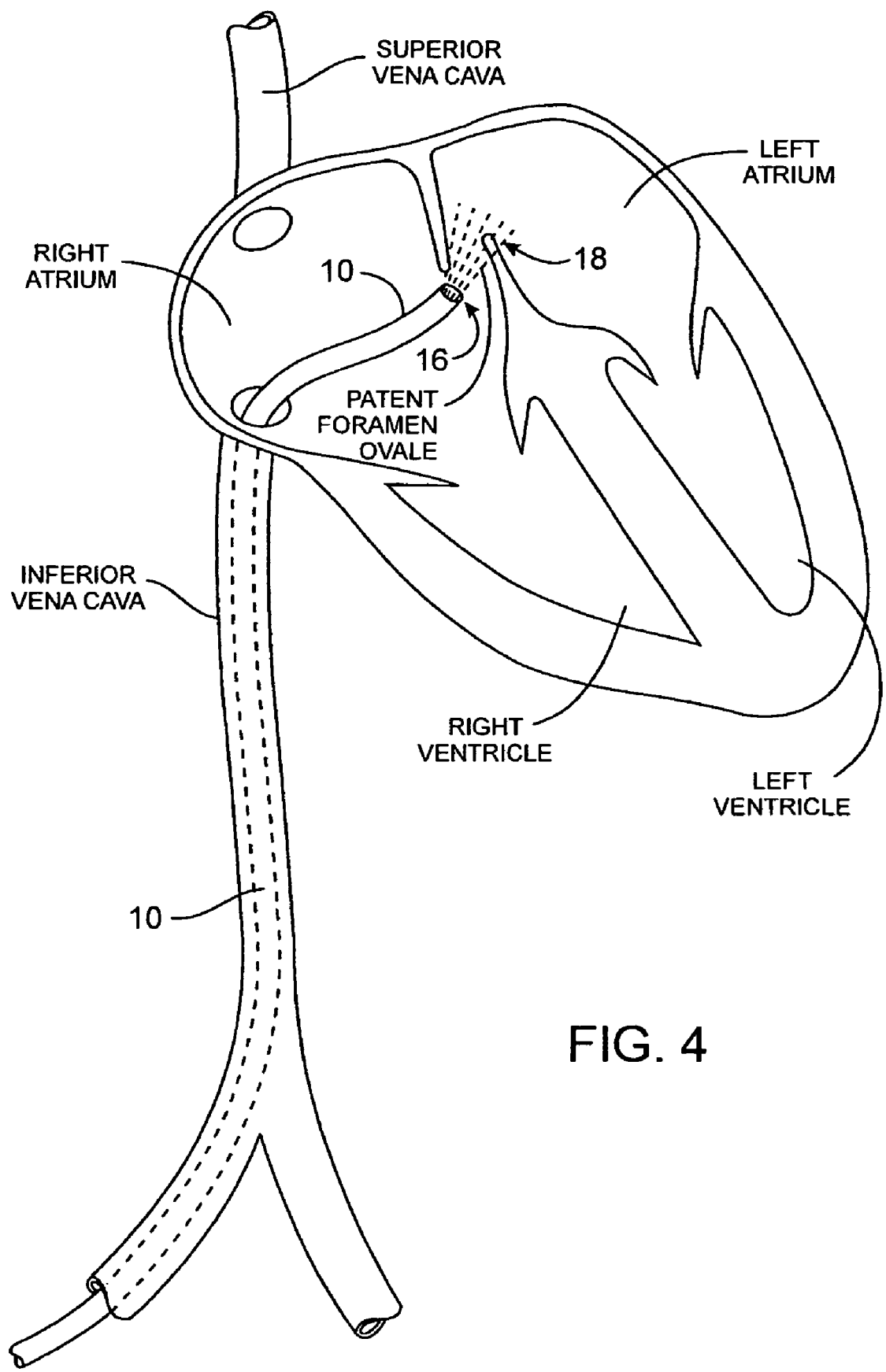
FIG. 4 is a diagram of a catheter apparatus having an energy transmission member according to one embodiment of the present invention, the catheter passing through the inferior vena cava and right atrium to position the end effector adjacent the patent foramen ovale.

Referring now to FIG. 4, another embodiment of catheter 10 includes at least one energy transmission member 16 at or near its distal end for transmitting energy 18 to tissue. The transmitted energy may include, for example, laser, ultrasound, radio frequency, microwave energy, cryogenic energy, the removal of energy via cooling, or any other suitable form of energy. Generally, energy 18 is used to disrupt, shrink, weld or traumatize tissue to evoke a tissue response that will lead to closure of the PFO. For example, scar tissue may be generated to close the PFO. In some embodiments, the energy transmission member may include one or more needles with or without abrasive surfaces. The needles may be inserted across or through the PFO or adjacent tissue to deliver the energy to the tissue. In some embodiments, the needles and their deployment system may be arranged to gather the tissue of the PFO together, for example axially or radially, before, during and/or after energy is applied to the tissue.

Figure 5:
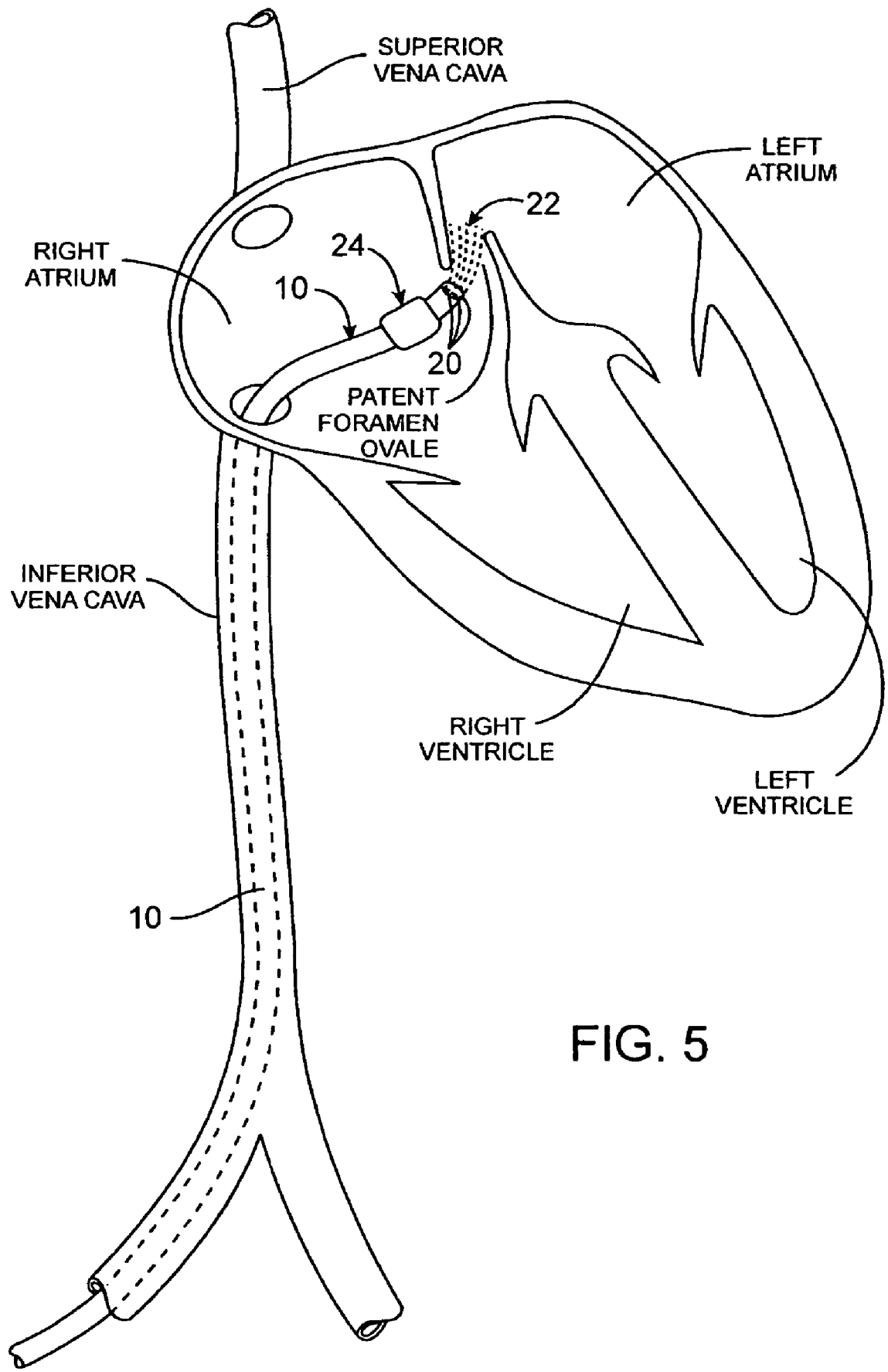
FIG. 5 is a diagram of a catheter apparatus having apertures for dispensing a fluid according to one embodiment of the present invention, the catheter passing through the inferior vena cava and right atrium to position the end effector adjacent the patent foramen ovale.

In yet another embodiment, and referring now to FIG. 5, catheter 10 may include one or more apertures 20 for allowing one or more biocompatible fluids 22 to be disposed from catheter 10. In some embodiments, a balloon 24 may be inflated at or adjacent the distal end of the catheter to slow or stop blood flow in the area of the PFO to increase the residence time of fluid(s) injected into the PFO. Various biocompatible and/or bioabsorbable fluids 22 may be used in various embodiments to invoke closure of a PFO. In some embodiments, for example, and acid or an adhesive may be used which will cause a local burning or scarring of the PFO tissue. However, as the fluid leaves the area of the PFO, it will be rapidly diluted by mixing with blood to a safe dilution, and will not cause harm to the patient by entering the patient's bloodstream. Biocompatible methacrylates, for example, may be used to effectively "glue" the PFO shut and at the same time trigger a healing response.

Apparatus and methods according to the present invention may rely on energy, in various forms, to seal the PFO, either with or without an associated implant. Implants, such as patches, self-closing elements, or the like, may be welded into place using energy in a variety of ways. In various embodiments, any suitable type or configuration of welding substance, matrix, patch or the like may be used to enhance application of energy for providing PFO closure. Devices and methods using various types of energy and tissue welding substances to close PFOs are described fully in U.S. patent application Ser. No. 10/665,974, which was previously incorporated by reference.

Figure 6A:
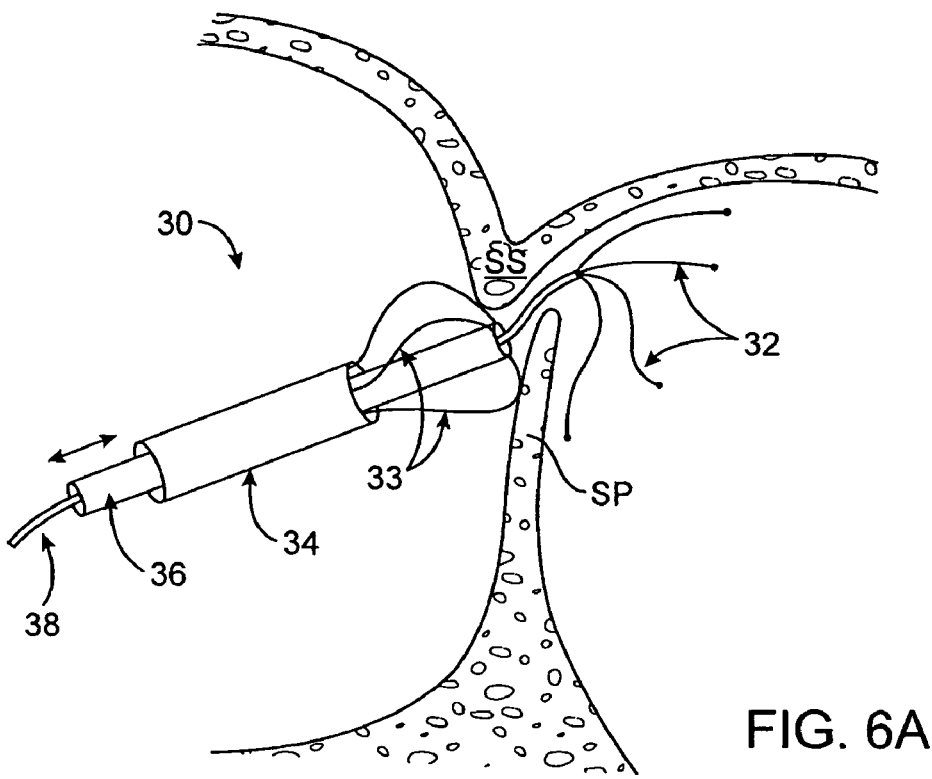
FIGS. 6A and 6B illustrate a catheter apparatus including a backstop and inflatable member for treating a PFO according to one embodiment of the present invention.
Figure 6B:
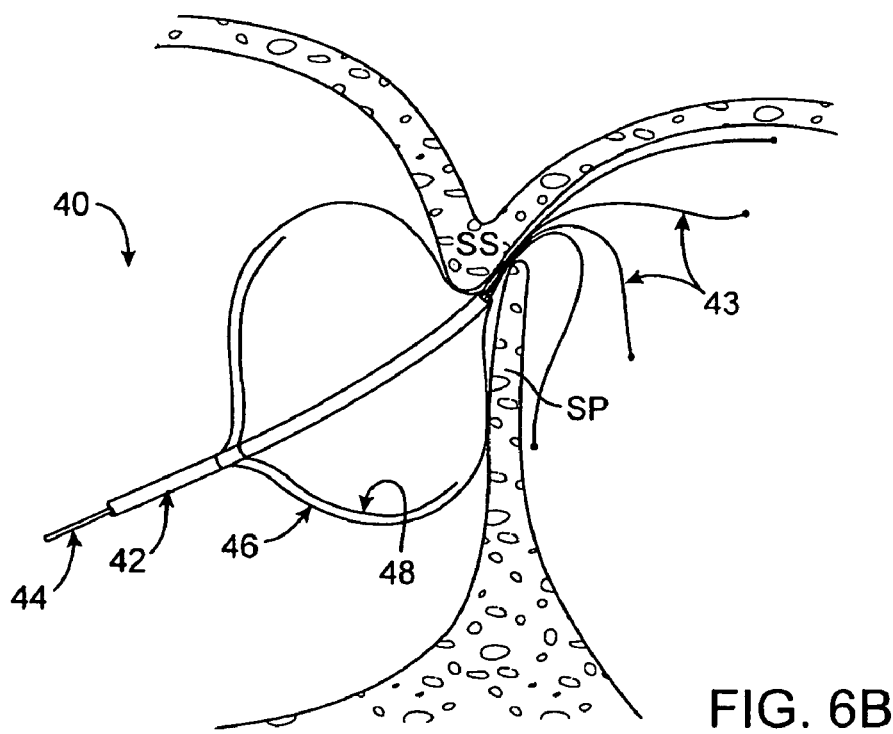

As an alternative to the implant-based devices, systems according to the present invention can function to weld the PFO closed with no implant left behind. As illustrated in FIGS. 6A and 6B, in some embodiments, a backstop and energy delivery catheter are placed in contact with the PFO, and energy is delivered to disrupt the collagen matrix of the primum and secundum to cause fusion of the two parts of the PFO. Energy used can be monopolar or bipolar RF (in which case the backstop acts as energy return, or ground electrode), ultrasound, laser, microwave, or resistance heating. Protein solder may be introduced to facilitate the weld.

Referring to FIG. 6A, one embodiment of a catheter device 30 for treating a PFO (the opening between the septum primum SP and septum secundum SS) may include an outer catheter shaft 34, an inner catheter shaft 36 slidably disposed within outer shaft 34, a backstop 32 coupled with a backstop actuator 38 extending through inner shaft 36, and energy delivery members 33. Energy delivery members 33 may deliver any suitable form of energy for providing PFO closure, such as but not limited to RF, ultrasound, laser or microwave energy. In some embodiments, backstop 32 may act as an energy return member, such as when bipolar RF energy is used.

As illustrated in FIG. 6B, an alternative embodiment of a catheter device 40 may include a catheter shaft 42, an expandable member 46, an energy delivery member 48 disposed within expandable member 46, and a backstop 43 coupled proximally with an actuator 44. Expandable member 46 and backstop 43 are used to position catheter device 40 in a desired location for treating the PFO, and energy is then applied via energy delivery member 48. In one embodiment, for example, energy delivery member may comprise an ultrasonic piezo-foil, though any other suitable delivery device may be used in alternate embodiments.

Figure 7A:
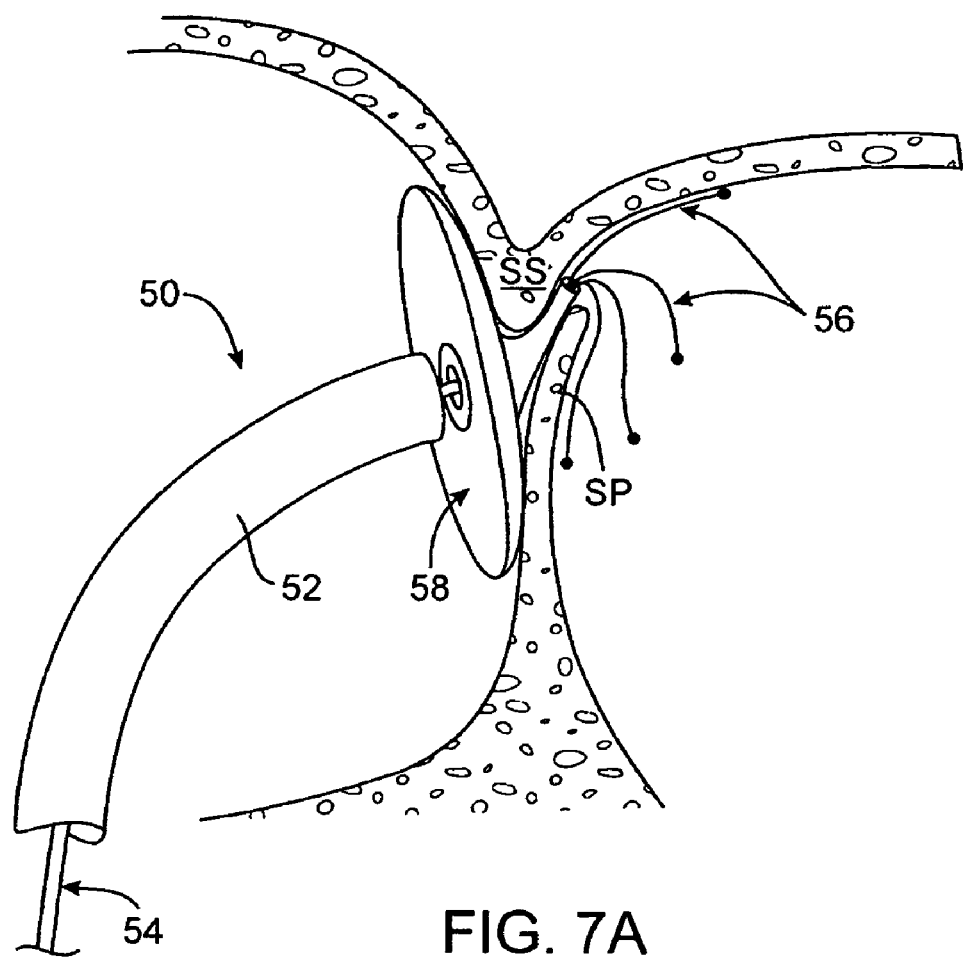
FIGS. 7A-7C illustrate a catheter apparatus including a "sombrero-shaped" PFO closure member according to one embodiment of the present invention.
Figure 7B:
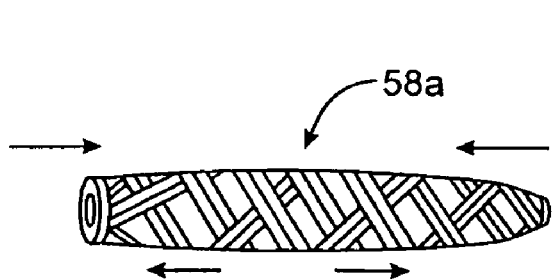
Figure 7C:
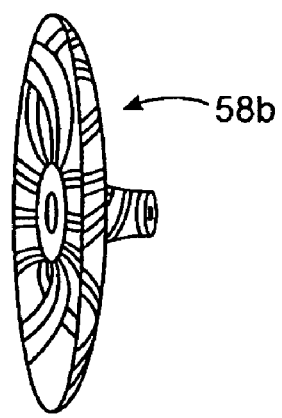

Another embodiment employing a backstop member is illustrated in FIGS. 7A-7E. As illustrated in FIG. 7A, one embodiment of a catheter device 50 for treating PFO may include a catheter shaft 52, a backstop 56 coupled proximally with an actuator 54, and a "sombrero-shaped" patch 58. Backstop 56 is used to help position catheter 50 and to bring tissues adjacent the PFO (such as septum primum SP and septum secundum SS) together. Patch 58 is then fixed in place against septum primum SP and septum secundum SS to cover the opening of the PFO. In some embodiments, the catheter device may include one or more energy transmission members for applying any suitable form of energy to weld or adhere patch 58 to tissues adjacent the PFO. In other embodiments, a tissue adhesive may be used. Other embodiments may used a locking tissue attachment mechanism for securing patch 58 to PFO tissue, as is discussed further below. Generally, as illustrated in FIGS. 7B and 7C, sombrero-shaped member 58 may be manipulated from a first, elongate shape 58a (FIG. 7B) to facilitate delivery through catheter shaft 52, to the sombrero shape 58b (FIG. 7C) that will allow patch 58 to cover the PFO opening. In one embodiment, patch 58 is made of a braided material to allow for translation from the elongate shape 58a to the sombrero shape 58b.

Figure 7D:
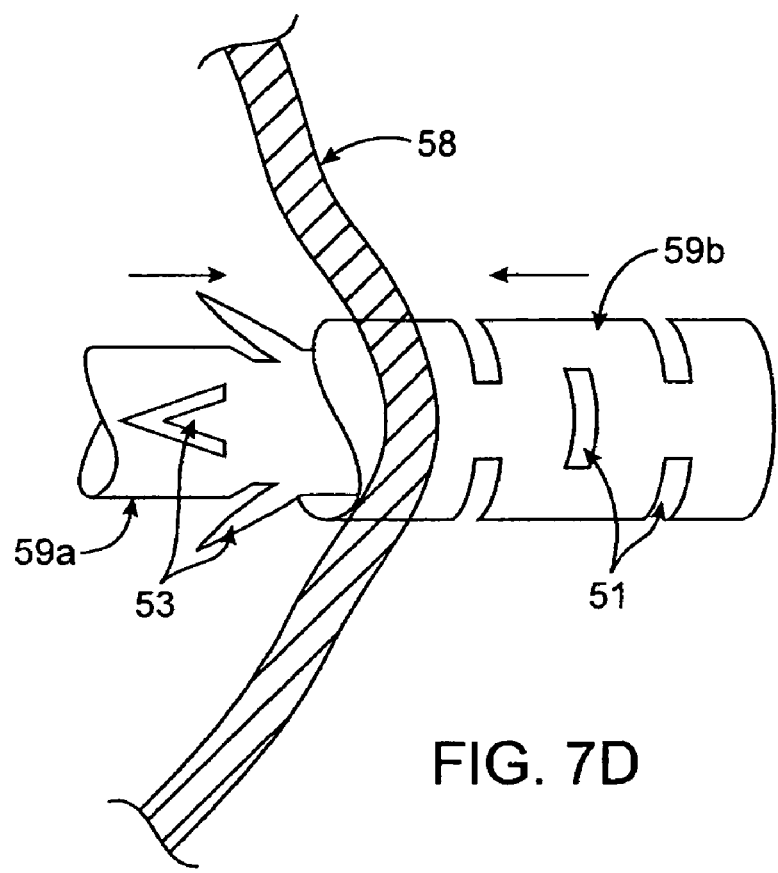
FIGS. 7D and 7E illustrate a locking mechanism for the sombrero-shaped member in FIGS. 7A-7C.
Figure 7E:
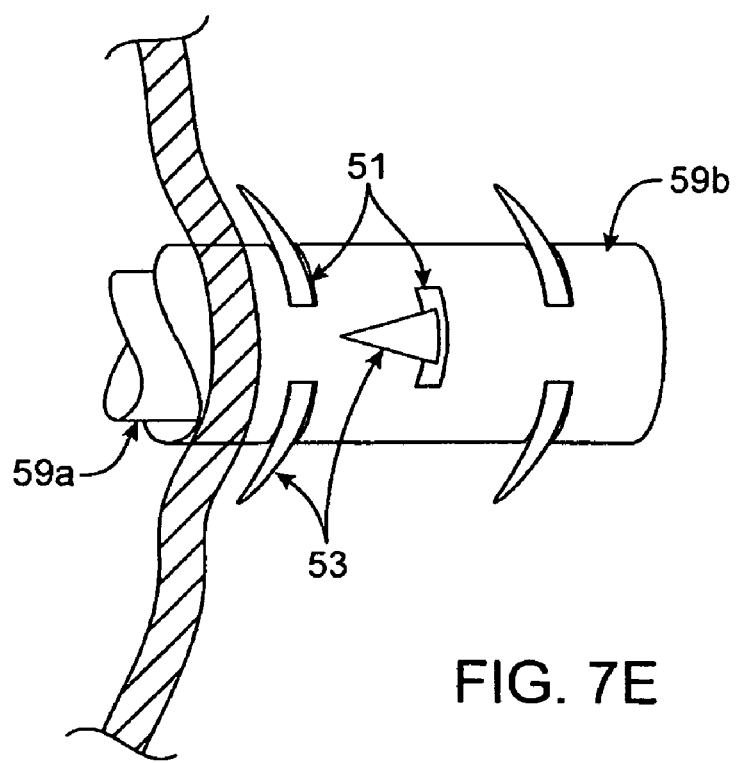

As shown in FIGS. 7D and 7E, one embodiment of catheter device 50 includes a locking distal end 59, which locks patch 58 into its sombrero-shaped configuration and also secures patch 58 to the PFO. An inner shaft 59a is moved distally relative to an outer shaft 59b, and/or outer shaft 59b is moved proximally (see solid-tipped arrows), so that protrusions 53 on inner shaft 59a lock into apertures 51 on outer shaft 59b. FIG. 7E shows the locking distal end 59 in its locked position. If distal end 59 is positioned within a PFO and then placed in its locked position, at least some protrusions 53 will penetrate into PFO-adjacent tissue to secure distal end 59 within the PFO, thus securing the location of patch 58 at the PFO opening.

In other embodiments, PFO closure systems according to the present invention may utilize one or more clips to close the PFO. Such systems can be divided into designs that involve both a right and left atrial component, and those that are right-sided only. While they are generally not energized, it may be desirable to add energy to any of these designs to facilitate adhesion and sealing.

Figure 8:
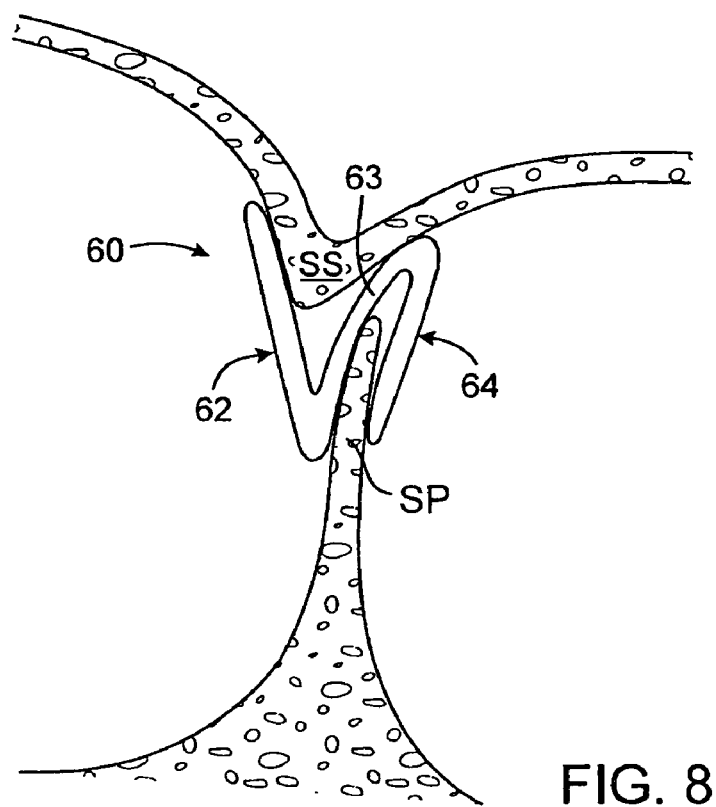
FIG. 8 shows a PFO closure device according to one embodiment of the present invention.

One embodiment of a right and left sided PFO clip 60 is illustrated in FIG. 8. In this embodiment, clip 60 generally has a Z or S shape, with a right atrial leg 62 disposed in the right atrium of the heart, a left atrial leg 64 in the left atrium, and a bridging leg 63 extending through the PFO to connect the other two legs. Clip 60 may be made of wire, for example, using any appropriate wire material, such as but not limited to nitinol, stainless steel, platinum, gold, tantalum, or combinations or alloys of any of these. In the embodiment shown, clip 60 is one continuous piece of wire, although many other configurations are contemplated according to alternative embodiments. Resorbable materials such as PLLA, PLGA, iron, magnesium alloys may be used as well. The resorbable materials may be engineered to create a vigorous inflammatory response to induce sealing of the PFO prior to erosion and resorption of the device. Typically, a delivery catheter is advanced through the PFO, left atrial leg 64 is deployed, the delivery device is pulled back into the right atrium, and right atrial leg 62 is deployed. Barbs, hooks or other fixation aids may be included.

In some embodiments, bridging leg 63 may comprise two or more parts, such as wire or the like, which spread apart from each other when deployed within the PFO. This spreading motion applies opposed lateral force to tissue at opposite sides of the PFO, thus widening the PFO laterally and bringing tissues between the two spreading members together. Any suitable clip or other PFO closure device described below may include one or more elements for applying such laterally-directed force, and some specific embodiments are described further below.

Figure 9A:
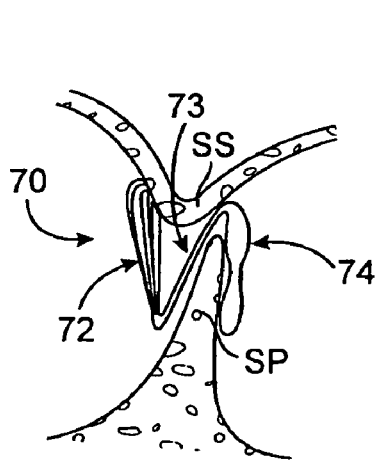
FIGS. 9A-9C illustrate another PFO closure device according to one embodiment of the present invention.
Figure 9B:
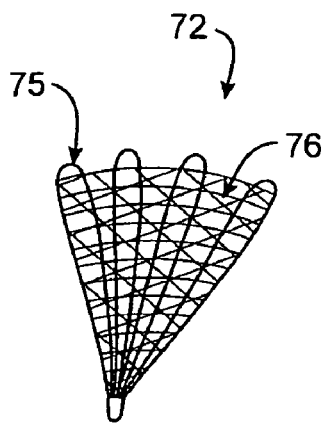
Figure 9C:
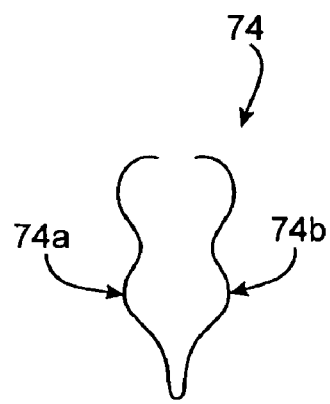

Referring now to FIGS. 9A-9C, another embodiment of a Z-shaped clip also includes a right atrial leg 72, left atrial leg 74 and bridging member 73. As shown in FIG. 9B, right atrial member 72 may include multiple wire loops 75 coupled with a mesh material 76. Together, loops 75 and mesh 76 act as a patch-like structure on the right side of the PFO. Left atrial member 74, as shown in FIG. 9C, may include a shaped wire. In some embodiments, left atrial member 74 may include two arms 74a, 74b. Arms 74a, 74b, when released from a delivery catheter, may move out laterally before moving toward and contacting the septum primum SP. In various embodiments, left atrial member 74 may be given any suitable shape, such that arms 74a, 74b move in one or more desired directions when released from a delivery catheter to better contact and hold septum primum SP. As in the previous embodiment, bridging member 73 may be configured to apply lateral force within the PFO to bring tissues together.

Figure 10A:
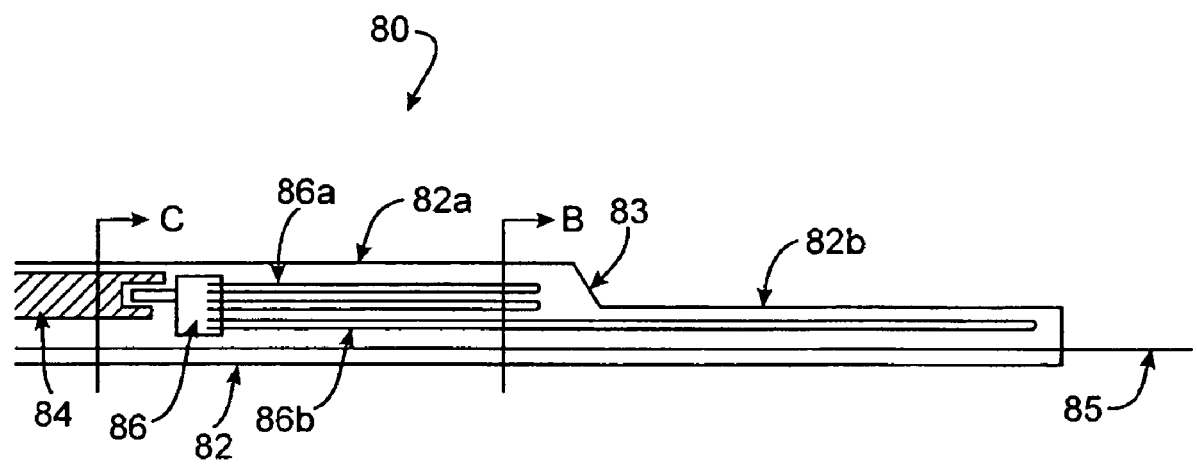
FIGS. 10A-10C illustrate a delivery catheter for a PFO closure device according to one embodiment of the present invention.

With reference now to FIG. 10A, a delivery catheter device 80 for delivering a clip such as that described by FIGS. 9A-9C is shown in longitudinal cross-section. Delivery device 80 in one embodiment may include a catheter shaft 82 having a proximal portion 82a and a distal portion 82b, and a pusher member 84 disposed within shaft 82. A clip 86 is loaded distal to pusher member 84 within shaft 82, and catheter device 80 may be delivered over a guidewire 85. In the embodiment shown, proximal portion 82a has a larger cross-sectional diameter that distal portion 82b and includes an aperture 83 at its distal end. Due to the configuration of delivery device 80, when pusher member 84 is advanced distally relative to catheter body 82, a right atrial leg 86a of clip 86 is released out of aperture 83 before a left atrial leg 86b of clip 86 is released. Such a delivery technique may sometimes be advantageous over techniques in which a left atrial leg is released before a right atrial leg. In some embodiments, delivery catheter 80 may also be used to remove clip 86 from the PFO and then reposition clip 86 in a more desirable position. Is such cases, advancing delivery catheter 80 over clip 86 may act to straighten and disengage clip 86. Due to the extended distal portion 82b of shaft 82, advancing catheter 80 over clip 86 may first straighten and disengage left atrial leg 86b and may then subsequently straighten and disengage right atrial leg 86a. Catheter 80 may then be withdrawn to remove clip 86 from the PFO, and may then be used to redeploy clip 86 in the PFO.

Figures 10B, 10C:
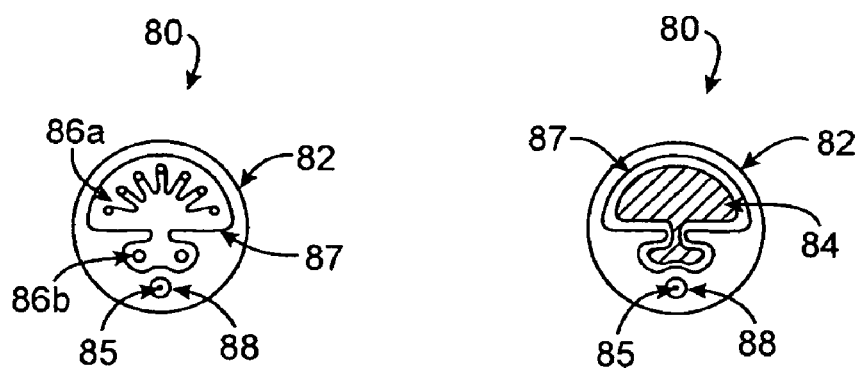

FIGS. 10B and 10C show delivery catheter device 80 in axial cross-section. FIG. 10B shows that catheter body 82 may include a clip delivery lumen 87 in which clip 86 is disposed, as well as a guidewire lumen 88 in which guidewire is disposed. Clip delivery lumen 87 may have any suitable shape and size for facilitating clip delivery. In the embodiment shown, clip delivery lumen 87 is one continuous lumen having compartments for right atrial leg 86a and left atrial leg 86b of clip. FIG. 10C shows that pusher member 84 is disposed in clip delivery lumen 87 proximal of clip 86.

An example of a right-side clip device is illustrated in FIGS. 11A-11F. Generally, -side clip devices deploy a normally closed expandable device which is introduced to the PFO, expanded, driven into the tissue of the septum primum SP and septum secundum SS, and allowed to return to its normally-closed position, closing the PFO. Expansion can be achieved with balloons or by mechanical means, and any previously mentioned clip material may be used.

Figure 11A:
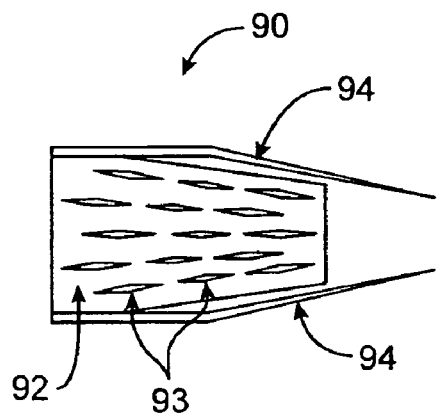
FIGS. 11A-11F illustrate a self-closing stent PFO closure device according to one embodiment of the present invention.
Figure 11B:
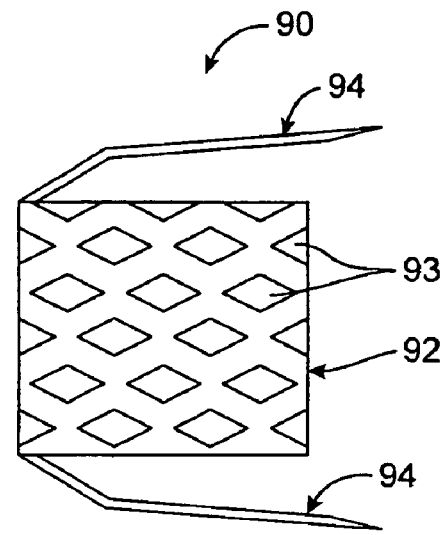

As shown in FIG. 11A, a clip device 90 may suitably include an expandable, self-closing stent 92 having multiple slits 93, and multiple tissue attachment members 94 coupled with stent 92. Stent 92 may be delivered via a catheter device to a location for treating a PFO in its unexpanded state, as shown in FIG. 11A. Stent 92 may then be expanded, as shown in FIG. 11B, to expand tissue attachment members 94. Tissue attachment members 94 are then advanced to pierce into septum primum SP and septum secundum SS tissue, and stent 92 is released from expansive force to allow it to close to its unexpanded form, thus pulling tissue attachment members 94 together, and thus bringing septum primum SP and septum secundum SS together.

Figure 11C:
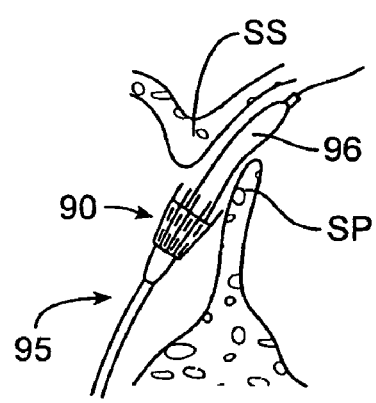
Figure 11D:
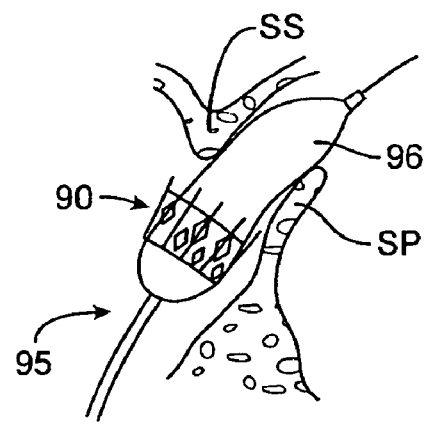
Figure 11E:
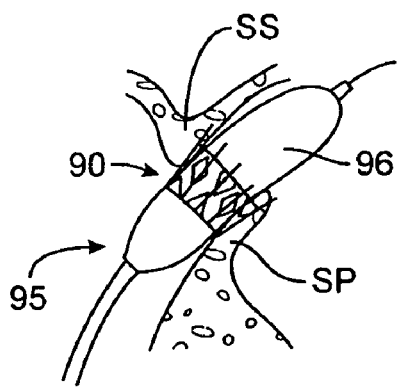
Figure 11F:
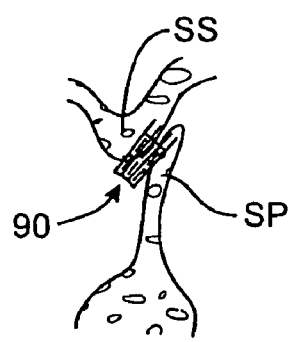

The technique just described is illustrated in FIGS. 11C-11F. FIG. 11C shows clip device 90 disposed in its unexpanded configuration over a delivery catheter 95 having an inflatable balloon 96. In FIG. 11D, balloon 96 has been inflated to expand clip device 90. As illustrated in FIG. 11E, clip device 90 is then driven into the PFO such that tissue attachment members 94 pierce and attach themselves to septum primum SP and septum secundum SS. Then, as shown in FIG. 11F, balloon 96 is deflated and withdrawn, allowing clip device 90 to return to its unexpanded configuration, thus pulling septum primum SP and septum secundum SS together to close the PFO.

Figure 12A:
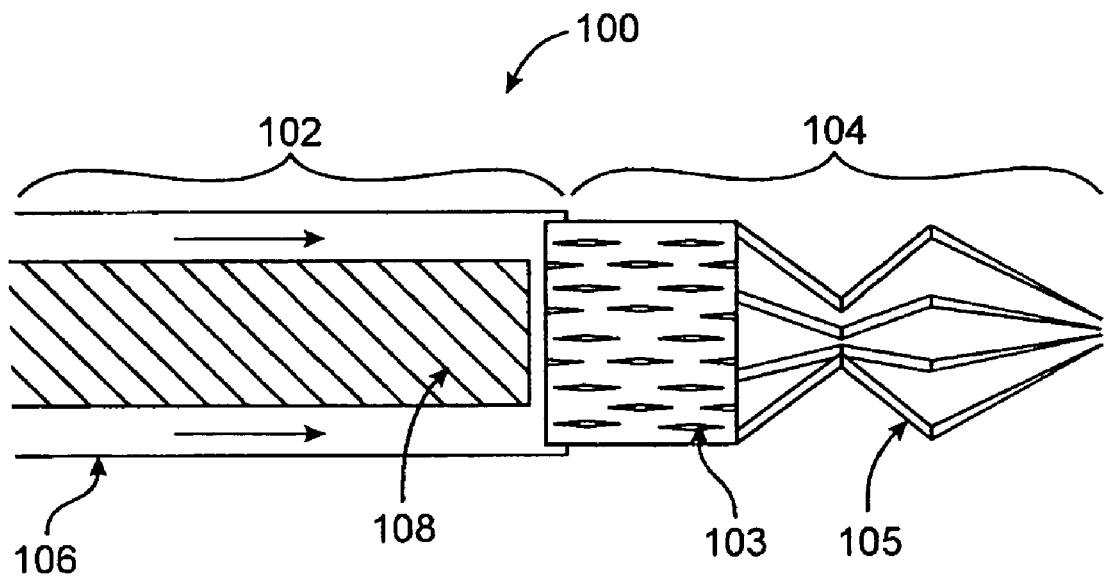
FIGS. 12A and 12B show another self-closing stent PFO closure device according to one embodiment of the present invention.
Figure 12B:
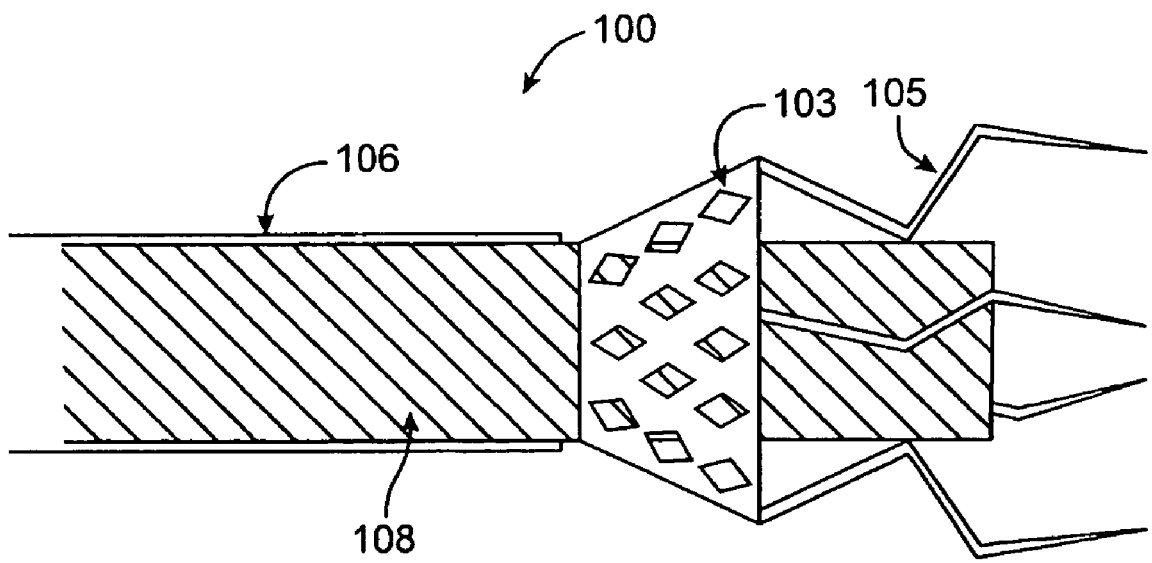

An alternative embodiment of the clip device just described is illustrated in FIGS. 12A and 12B. In this embodiment, a PFO closure system 100 includes a delivery catheter 102 and a clip device 104. Delivery catheter 102 includes in outer shaft 106 and an inner shaft 108 slidably disposed within outer shaft 106. In some embodiments, delivery catheter 102 may be advanced into/through a PFO over a guidewire. Clip device 104 includes an expandable stent 103 coupled with multiple tissue attachment members 105. As illustrated by the solid-tipped arrows in FIG. 12A, inner shaft may 108 may be advanced distally relative to outer shaft 106. As shown in FIG. 12B, inner shaft 106 may be further advanced to extend through stent 103 and push apart tissue attachment members 105, thus expanding stent 103. Tissue attachment members 105 may then be driven into tissue adjacent a PFO, and inner shaft may be withdrawn to allow stent 103 to close down to its unexpanded state, thus pulling together the PFO tissues via tissue attachment members 105.

Figure 13A:
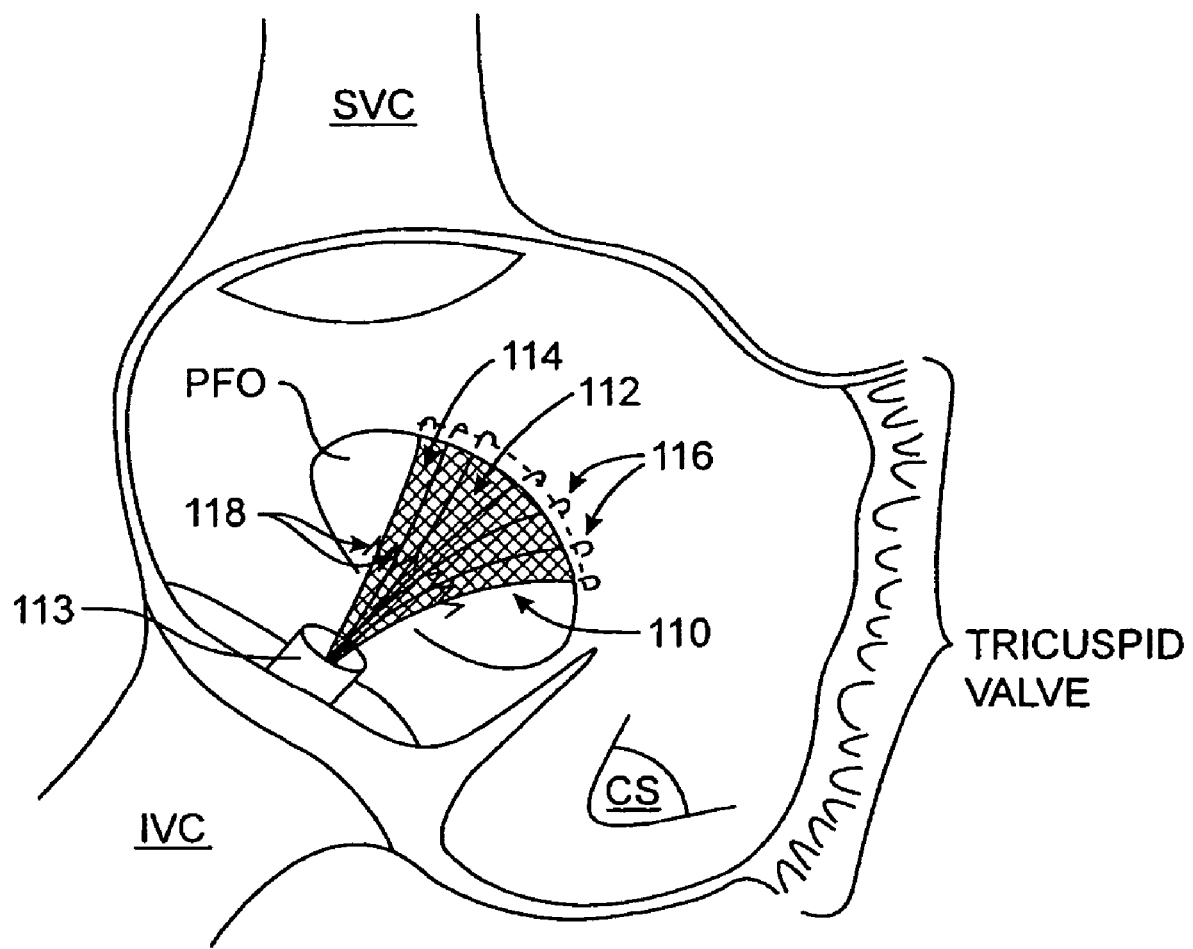
FIGS. 13A and 13B show a patch PFO closure device according to one embodiment of the present invention.
Figure 13B:
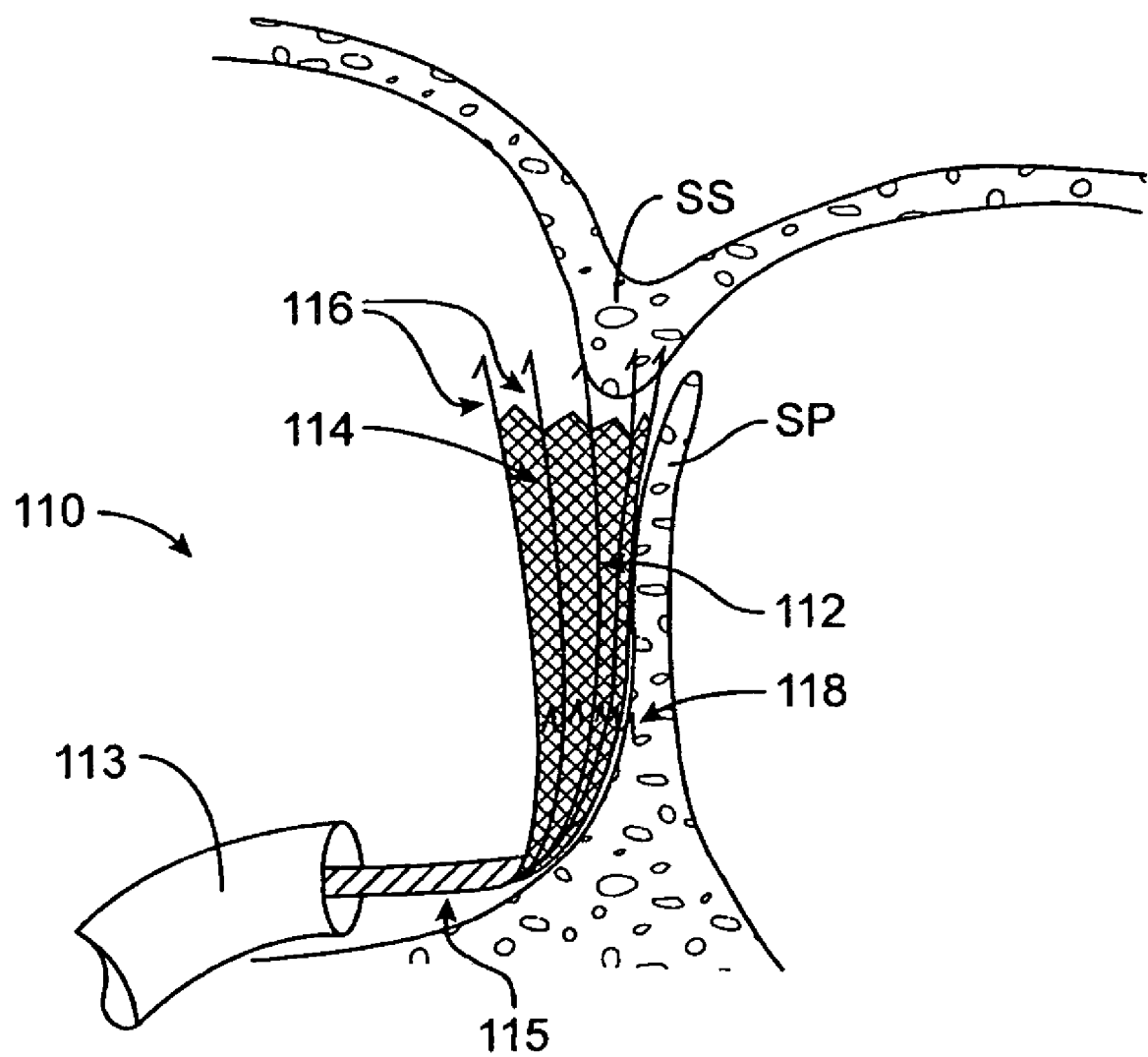

With reference now to FIGS. 13A and 13B, in one embodiment a PFO closure device 110 is configured so as to act as a patch. Closure device 110 includes multiple wires 112 such as wires described above, a mesh 114 or other matrix coupled with wires 112, proximal hooks 118 and distal hooks 116. A catheter device 113 may be used to deliver closure device 110 through a suitable vessel, such as the inferior vena cava 113. (Other labeled anatomical references are the superior vena cava SVC and coronary sinus CS.) As shown in FIG. 13B, closure device 110 may be advanced out of catheter device 113 using a pusher rod 115 (or any other suitable mechanism in alternative embodiments), such that distal hooks 116 contact and attach to septum secundum SS and proximal hooks 118 secure themselves to septum primum SP. The network of wires 11.2 and mesh 114 then act as a patch to seal the PFO.

It will often be desirable to use ultrasound to view the device after deployment. It is possible to coat all of the devices described above with a biocompatible coating in which microbubbles of air or inert gas are captured within the coating, rendering them more visible under ultrasound. In the case of degradable polymers, it will be possible to introduce microbubbles into the material during the extrusion process.

Figure 14A:
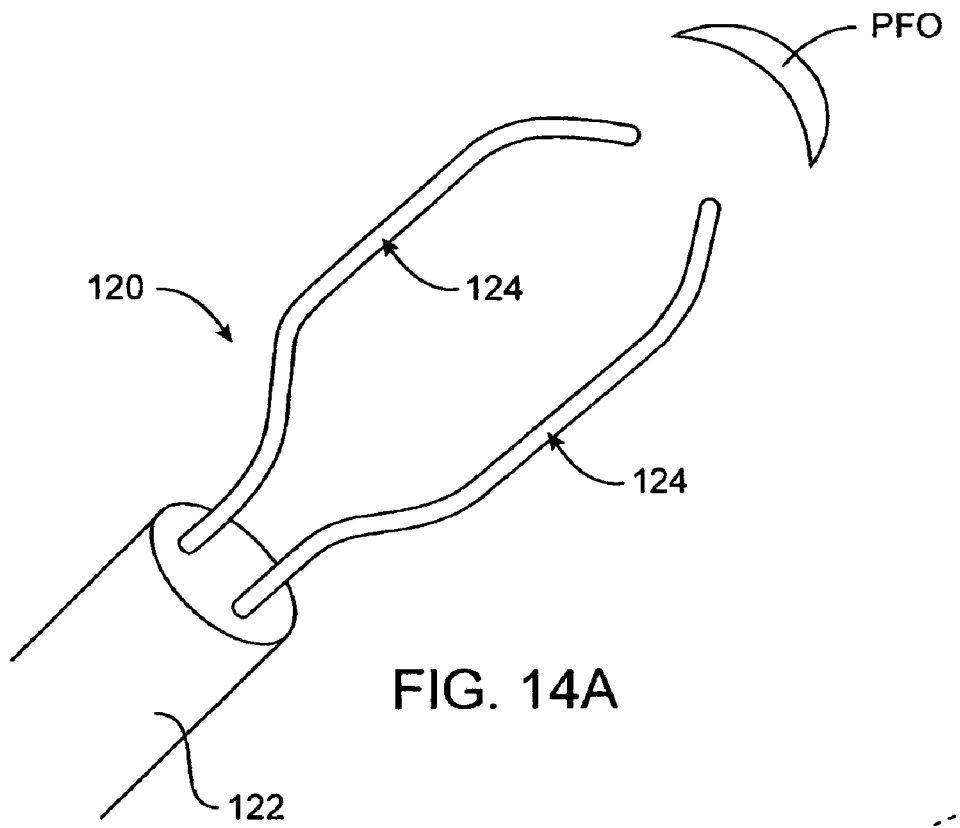
FIGS. 14A and 14B show a "fish mouth" PFO closure device according to one embodiment of the present invention.
Figure 14B:
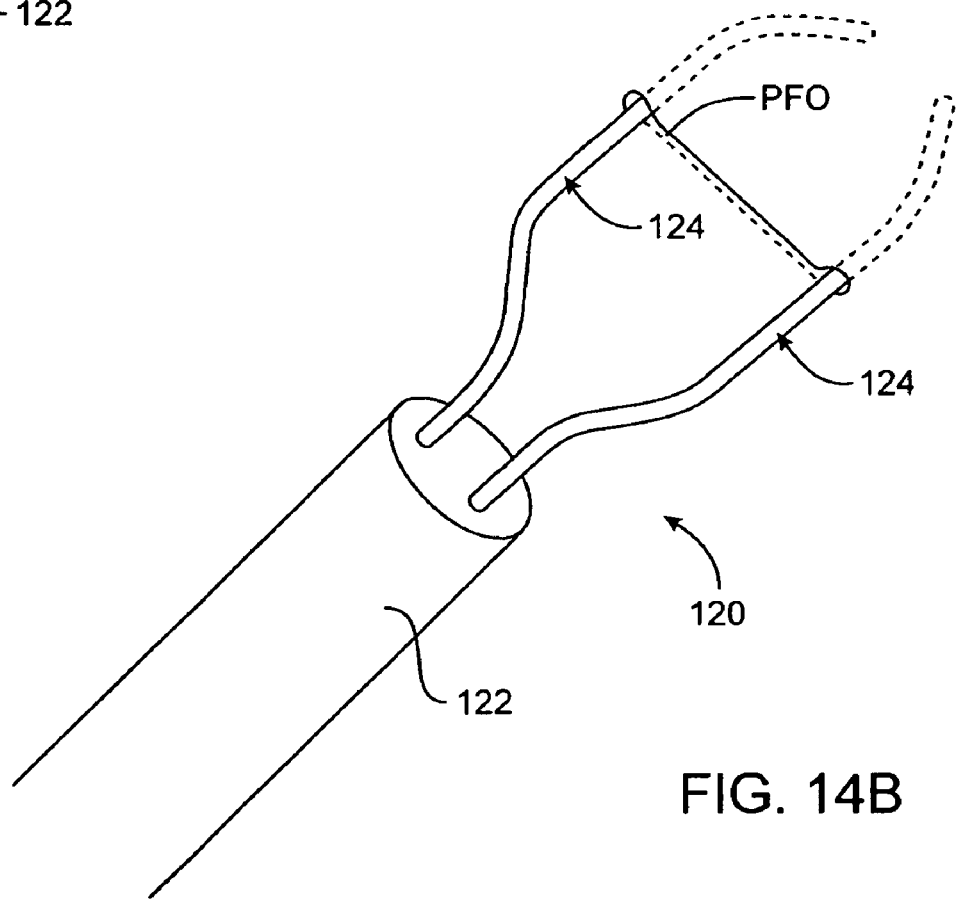

Referring now to FIGS. 14A and 14B, one embodiment of a PFO closure device 120 comprises a catheter 122 and a pair of flexible spring arms 124 attached to catheter 122. Lateral force serves two purposes: it rotationally orients a delivery catheter relative to the PFO, and it brings together the septum primum and septum secundum and positions the PFO in its naturally closed position. Once it is held in its naturally closed position, as shown in FIG. 14B, a penetrating staple, non-penetrating clip or other suitable device may be applied to permanently hold together and seal the PFO. Additionally, the lateral spring arms might be used to bring the primum and secundum together to be welded together by any of the energy delivery mechanisms previously described, with or without protein solder, in order to close the PFO.

Figure 15A:
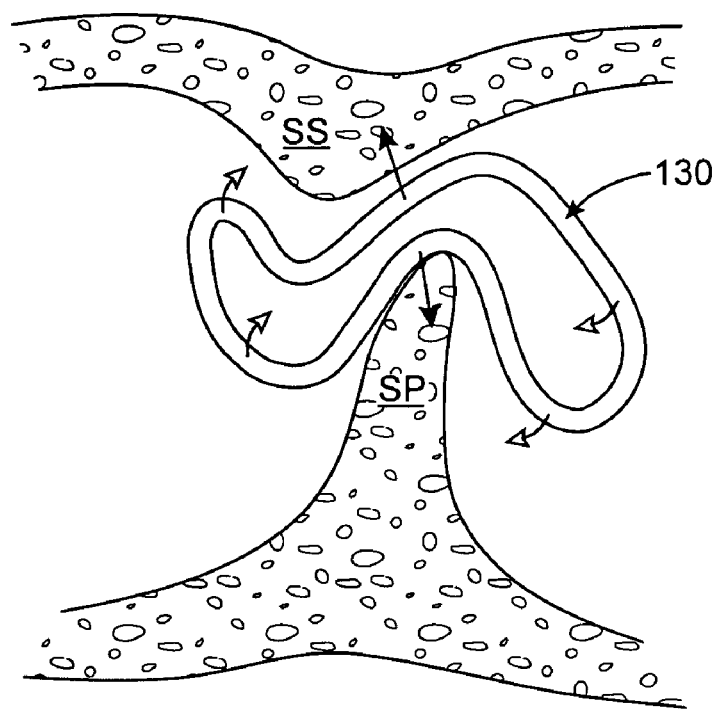
FIGS. 15A and 15B illustrate alternative embodiments of a fish mouth PFO closure device according to two embodiments of the present invention.
Figure 15B:
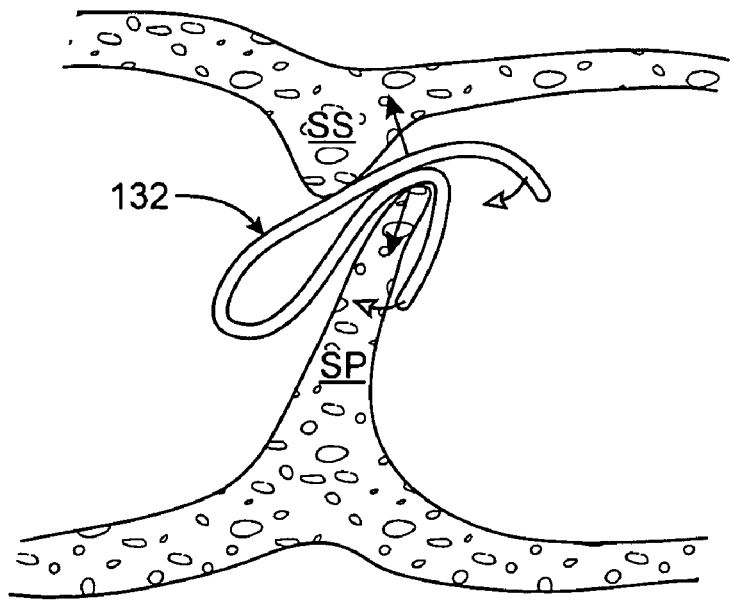

With reference now to FIGS. 15A and 15B, some embodiments of devices for applying lateral force in a PFO include lateral force clips. In FIG. 15A, the clip 130 is a continuous piece of wire, metal or any other suitable material, and is configured to apply not only lateral force (solid-tipped arrows) but also force against septum primum SP and septum secundum SS (hollow-tipped arrows). In an alternative embodiment, shown in FIG. 15B, an open-ended clip 132 applies lateral force (solid-tipped arrows) and force against the septum primum SP (hollow-tipped arrows).

Figure 16A:
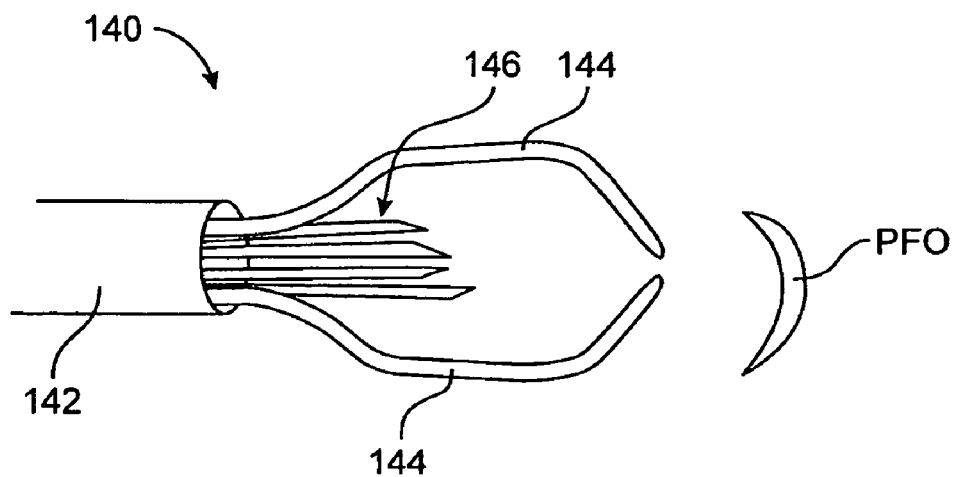
FIGS. 16A-16C illustrate a fish mouth PFO closure device with clip application according to one embodiment of the present invention.
Figure 16B:
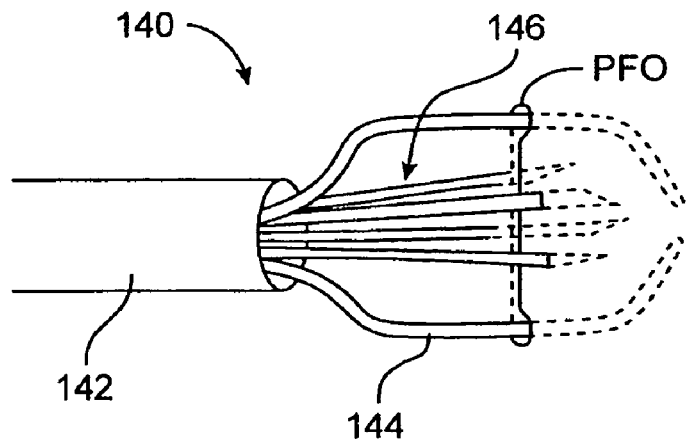
Figure 16C:
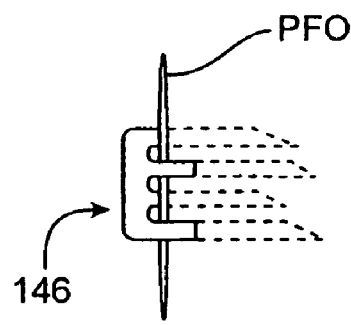

Referring now to FIGS. 16A-16C, one embodiment of a PFO closure device 140 includes a catheter 142 and a pair of flexible spring arms 144 coupled with catheter 142. Disposed within and deployable from catheter body is a staple device 146 (or clip device) for attaching to tissues adjacent a PFO. FIG. 16B shows device 140 with arms 144 disposed within the PFO and thus applying lateral force within the PFO to bring adjacent tissues together. Staple device 146 is then delivered either by the same or a second catheter. Staple device 146 penetrates (dotted lines in FIG. 16B) and pulls together the surfaces of the primum and secundum, which form the PFO. Staple device 146 might also have mechanical features, such as barbs or needles, or be made from materials, which invoke a healing response to promote the primum and secundum to heal together. Instead of a pair of flexible spring arms 144, catheter 142 may alternatively include a pair of arms, the distance between which is controlled via a mechanism in the handle of catheter 142. In some embodiments, arms 144 may be coupled with one or more pieces of staple device 146 (or other closure device), such that when arms move apart from one another, they spread staple device apart as well. This spreading of staple device may help provide for equivalent spacing of the various staple projections, so that PFO tissue is secured at regular intervals across the width of the PFO. After staple device is deployed into tissue, catheter 142 and arms 144 are removed from the PFO, leaving staple device 146 in place, as shown in FIG. 16C. In an alternative embodiment, rather than deploying staple device 146 which penetrates tissue, a non-penetrating clip device may be deployed.

Figure 17A:
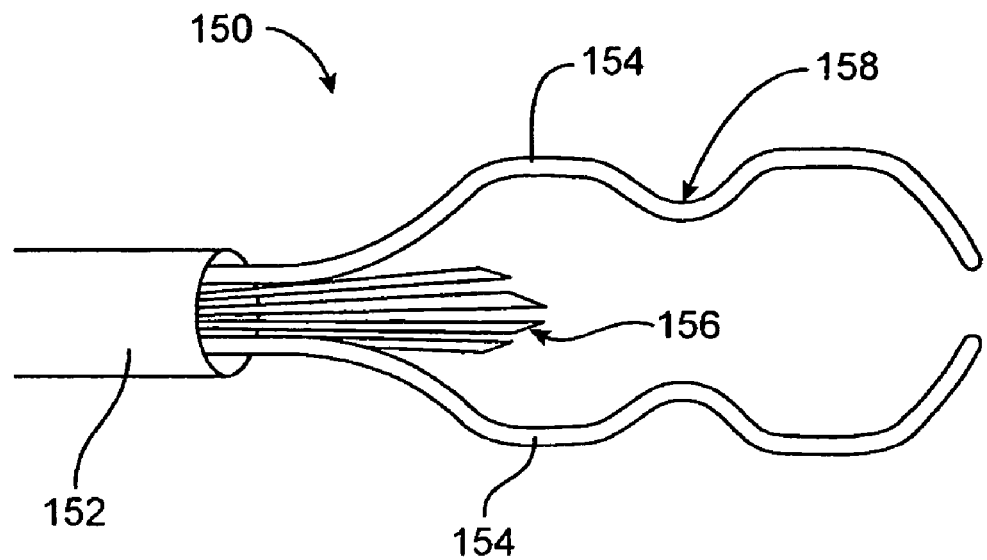
FIGS. 17A and 17B show alternative embodiments of a fish mouth PFO closure device with clip application according to two embodiments of the present invention.
Figure 17B:
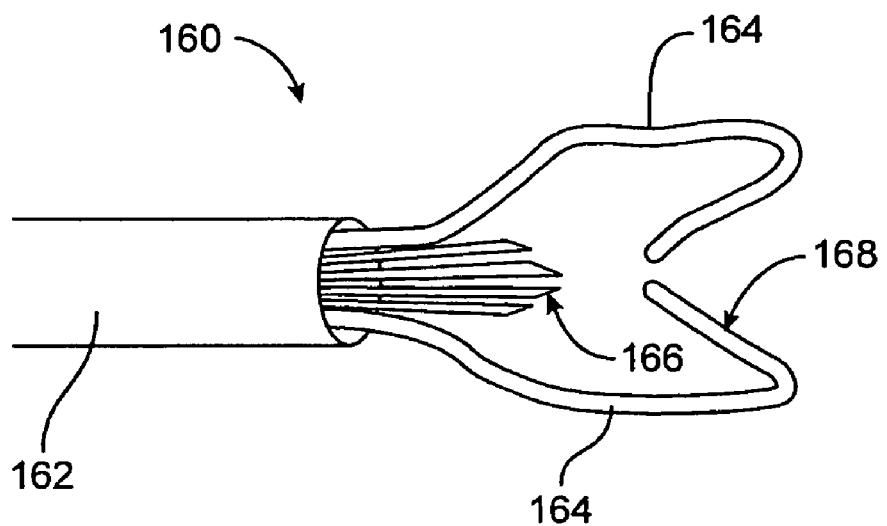

Alternate embodiments of lateral force staple applier systems are shown in FIGS. 17A and 17B. In FIG. 17A, a PFO closure device 150 includes a catheter 152, flexible spring arms 154 and a staple device 156. In this embodiment, spring arms 154 include a shaped feature 158 that locks into the tunnel of the PFO to facilitate positioning of device 150 before deploying staple device 156. In another embodiment, as shown in FIG. 17B, a closure device 160 again includes a catheter, flexible spring arms 164 and a staple device 166. In this embodiment, spring arms 164 include hooked features 168 to hook over the septum primum to act as a backstop from within the left atrium. Any other suitable configuration for such flexible spring arms is contemplated within the scope of the invention.

An implant having spring force and at least partially located in the PFO is another method to apply the force required to bring together and secure the primum and secundum surfaces of the PFO. The implant may comprise any material, metal or plastic, which is capable of providing a preset spring force. The implant is delivered via a catheter. The implant might also have features, which cause a healing response. Examples of such spring force implants (referred to generally as "clips") are illustrated in FIGS. 18-21. Such clips are typically delivered via catheter to become attached to septum primum SP and septum secundum SS tissue.

Figure 18:
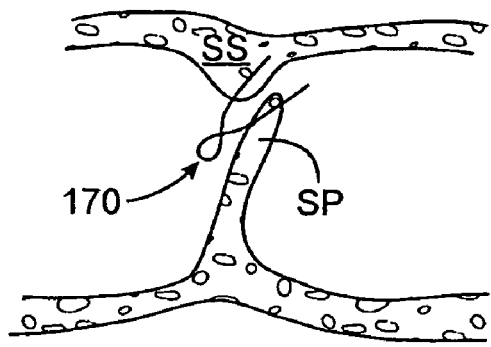
FIG. 18 illustrates a PFO clip according to one embodiment of the present invention.
Figure 19:
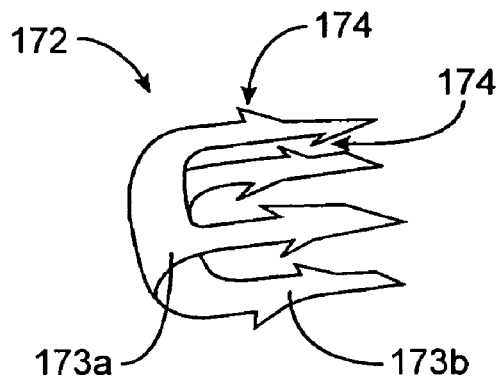
FIG. 19 illustrates a PFO clip according to another embodiment of the present invention.
Figure 20:
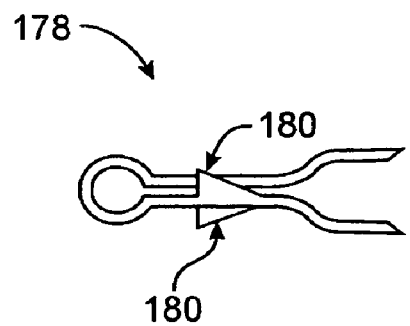
FIG. 20 illustrates a PFO clip according to another embodiment of the present invention.
Figure 21:
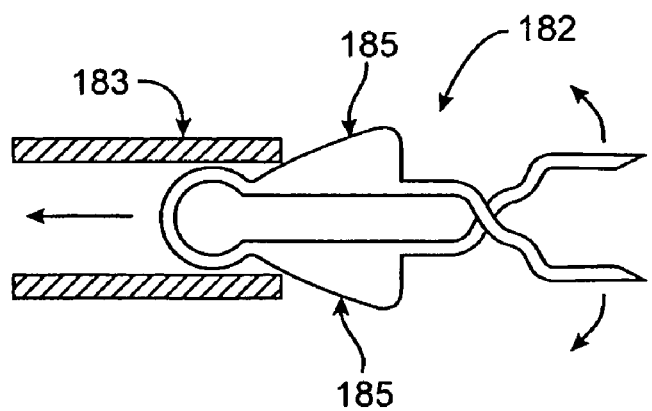
FIG. 21 illustrates a PFO clip according to another embodiment of the present invention.
Figure 22A:
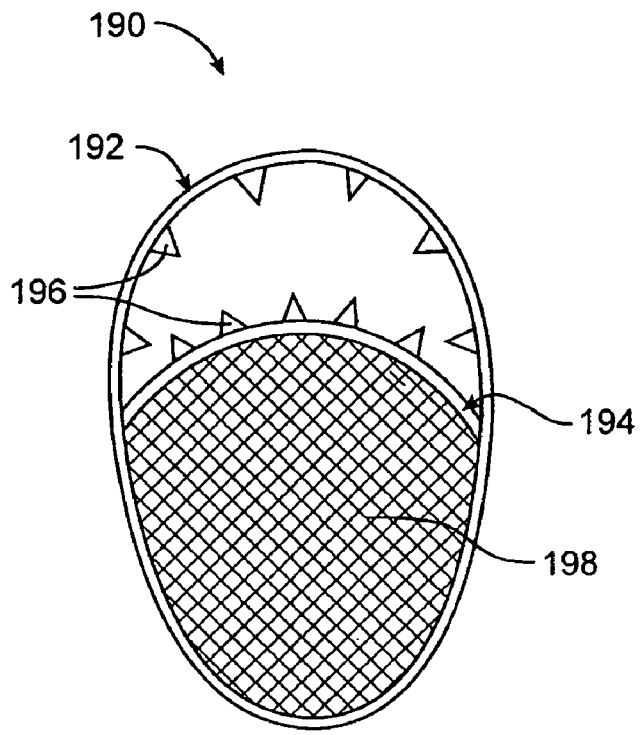
FIGS. 22A and 22B show a PFO closure patch device for attachment to the limbus of the fossa ovalis according to one embodiment of the present invention.
Figure 22B:
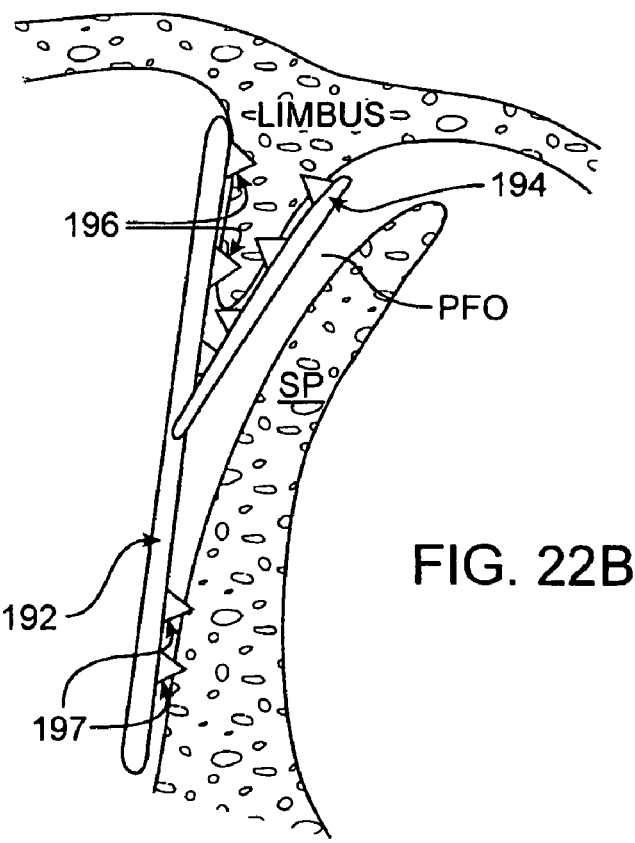

Referring to FIG. 18, a simple spring clip 170 attaches to septum secundum SS and septum primum SP and draws the tissues together. As in FIG. 19, another embodiment of a spring clip 172 may include an upper portion 173a and a lower portion 173b and may include attachment features such as barbs 174. In another embodiment, as in FIG. 20, a spring clip 178 may have an hourglass shape with retention barbs 180. In yet another embodiment, as illustrated in FIG. 21, a spring clip 182 may include release features 185 for facilitating release of clip 182 from a delivery catheter 183. When clip 182 is pulled back into delivery catheter 183 (solid-tipped arrow), the tines of clip 182 expand apart, due to release features 185. When clip 182 is advanced into tissue, the tines come together from their expanded configuration to not only pierce tissue but to clasp or pinch the tissue together between the tines. In other embodiments, the catheter itself may include one or more features for facilitating clip placement. In one embodiment, for example, inflatable balloons on the internal surface of a catheter may be expanded to squeeze a clip to deploy it out the end of the catheter. Many other delivery systems are contemplated in various embodiments.

In another embodiment, a staple device or clip device 190 having a patch 198 and a jaw with teeth 196 is secured to the limbus of fossa ovalis. Clip device 190 may include a right atrial wire frame 192 and an opposed jaw member 194, in some embodiments made of the same wire material. Teeth 196, barbs, hooks, staples or like are attached to wire frame 192 and jaw member 194 so as to attached device 190 to the limbus. Wire frame 192 and patch 198 then hang down over the PFO to close it. In some embodiments, a portion of clip device 190 may also be anchored to the septum primum, such as by additional teeth 197 or other features such as barbs, hooks or the like. Features of clip device 190, such as teeth 196, 197 staple legs or barbs, penetrate the limbus of fossa ovalis to secure the synthetic patch 198 over the PFO. Furthermore, the geometry of clip device 190 assists in correctly positioning it relative to the PFO.

Figure 23A:
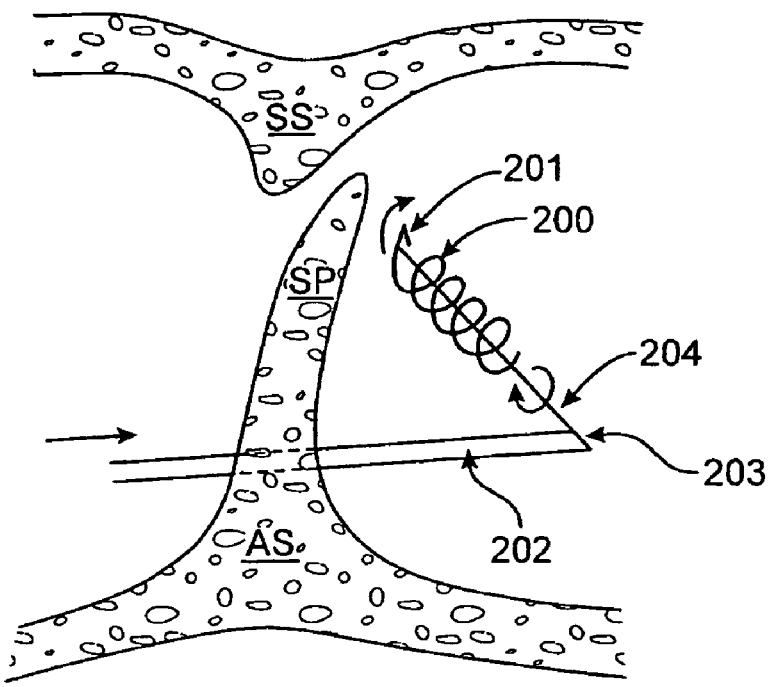
FIGS. 23A and 23B illustrate a spiral needle PFO closure device according to one embodiment of the present invention.
Figure 23B:
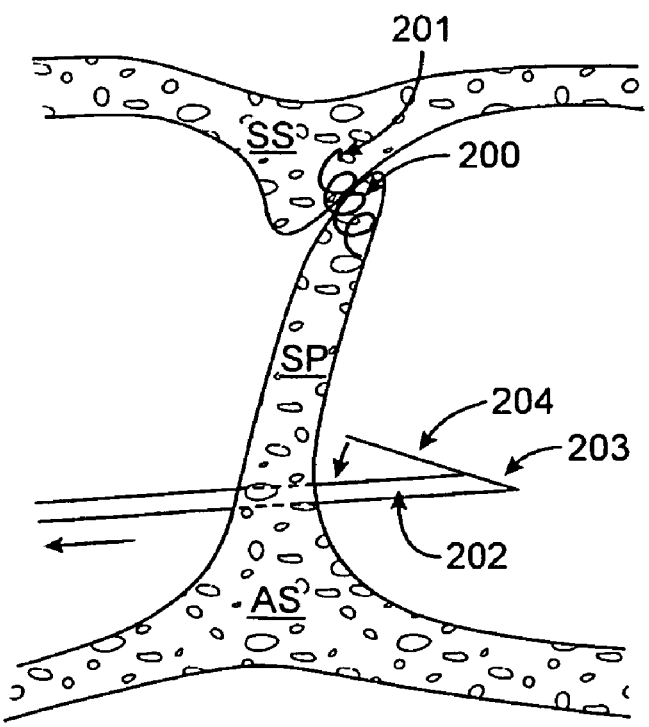

Referring now to FIGS. 23A and 23B, in another embodiment a PFO a spiral needle 200 may be applied to tissue adjacent the PFO to close the PFO, from a position within the left atrium. As shown in FIG. 23A, in one embodiment, a catheter 202 is delivered through the atrial septum AS, with spiral needle 200 and a retractable delivery arm 204 retracted within catheter 202. Once a distal portion of catheter 202 is positioned in the left atrium, delivery arm 204 may be extended from catheter 202 about a universal joint 203. Catheter 202 may then be turned, twisted or torqued to drive spiral needle 200 off of delivery arm 204 and into tissue adjacent the PFO. In one embodiment, as shown, spiral needle 200 is driven into and through septum primum SP tissue and into septum secundum SS tissue to bring the two tissues together. A hook or barb 201 on spiral needle 200 helps hold needle 200 in place within tissue. As shown in FIG. 23B, when spiral needle 200 is in place, it pulls together septum primum SP and septum secundum SS. Retractable delivery arm 204 is then retracted within catheter 202, and catheter 202 is withdrawn.

Although the foregoing description is complete and accurate, it has described only a few embodiments of the invention. Various changes, additions, deletions and the like may be made to one or more embodiments of the invention without departing from the scope of the invention. Additionally, different elements of the invention could be combined to achieve any of the effects described above. Thus, the description above is provided for exemplary purposes only and should not be interpreted to limit the scope of the invention as set forth in the following claims.

What is claimed is:

1. A method of treating a patent foramen ovale in a heart, the method comprising:
   advancing a closure device coupled with a distal end of a catheter device at least partway through the patent foramen ovale;
   releasing the closure device from the distal end of the catheter to induce closure of the patent foramen ovale without penetrating tissues adjacent the patent foramen ovale,
   wherein a portion of the released closure device disposed within the patent foramen ovale applies lateral force against tissues at opposite sides of the patent foramen ovale to bring tissue between the sides together, and
   deploying a staple to penetrate tissues adjacent the patent foramen ovale to seal the patent foramen ovale.

2. A method of treating a patent foramen ovale in a heart, the method comprising:
   advancing a closure device comprising flexible spring arms coupled with a distal end of a catheter device through tissue adjacent the patent foramen ovale;
   releasing the closure device from the distal end of the catheter to induce closure of the patent foramen ovale without penetrating tissues adjacent the patent foramen ovale,
   wherein the released closure device applies lateral force against tissues at opposite sides of the patent foramen ovale, apposing septum primum and septum secundum tissue of the patent foramen ovale to close the patent foramen ovale, and
   deploying a staple to penetrate tissues adjacent the patent foramen ovale to seal the patent foramen ovale.

3. A method as in claim 2, wherein the closure device is advanced through septum secundum tissue adjacent the patent foramen ovale.

4. A method as in claim 2, wherein the closure device is advanced through tissue of the atrial septum.

5. A method as in claim 4, wherein advancing the closure device comprises advancing the catheter device from a right atrium of the heart across the atrial septum to a left atrium of the heart.

6. A method as in claim 5, wherein advancing he closure device further comprises advancing the closure device from the left atrium of the heart into tissues of the patent foramen ovale.

7. A method as in claim 1, further comprising a pair of flexible spring arms, wherein the pair of arms are adapted to move apart from each other.

8. A method as in claim 7, further comprising a staple device coupled with the arms, such that the staple device is deployed when the arms move apart from each other.

9. A method as in claim 2, wherein the closure device is advanced through septum primum tissue adjacent the patent foramen ovale.

10. A method as in claim 2, further comprising a pair of flexible spring arms, wherein the pair of arms are adapted to move apart from each other.

11. A method as in claim 10, further comprising a staple device coupled with the arms, such that the staple device is deployed when the arms move apart from each other.

12. A method of treating a patent foramen ovale in a heart, the method comprising:
advancing a closure device coupled with a distal end of a catheter device at least partway through the patent foramen ovale;
releasing the closure device from the distal end of the catheter to induce closure of the patent foramen ovale without penetrating tissues adjacent the patent foramen ovale,
wherein a portion of the released closure device disposed within the patent foramen ovale applies lateral force against tissues at opposite sides of the patent foramen ovale to bring tissue between the sides together, and
deploying a non-penetrating clip adjacent the patent foramen ovale to seal the patent foramen ovale.

13. A method as in claim 12, further comprising a pair of flexible spring arms, wherein the pair of arms are adapted to move apart from each other.

14. A method as in claim 13, wherein said non-penetrating clip is deployed when the arms move apart from each other.

15. A method of treating a patent foramen ovale in a heart, the method comprising:
advancing a closure device comprising flexible spring arms coupled with a distal end of a catheter device through tissue adjacent the patent foramen ovale;
releasing the closure device from the distal end of the catheter to induce closure of the patent foramen ovale without penetrating tissues adjacent the patent foramen ovale,
wherein the released closure device applies lateral force against tissues at opposite sides of the patent foramen ovale, apposing septum primum and septum secundum tissue of the patent foramen ovale to close the patent foramen ovale, and
deploying a non-penetrating clip adjacent the patent foramen ovale to seal the patent foramen ovale.

16. A method as in claim 15, wherein the closure device is advanced through septum primum tissue adjacent the patent foramen ovale.

17. A method as in claim 15, wherein the closure device is advanced through septum secundum tissue adjacent the patent foramen ovale.

18. A method as in claim 15, wherein the closure device is advanced through tissue of the atrial septum.

19. A method as in claim 18, wherein advancing the closure device comprises advancing the catheter device from a right atrium of the heart across the atrial septum to a left atrium of the heart.

20. A method as in claim 18, wherein advancing the closure device further comprises advancing the closure device from the left atrium of the heart into tissues of the patent foramen ovale.

21. A method as in claim 15, further comprising a pair of flexible spring arms, wherein the pair of arms are adapted to move apart from each other.

22. A method as in claim 21, wherein said non-penetrating clip is deployed when the arms move apart from each other.

* * * * *